US012558403B2

(12) United States Patent
Zhang et al.

(10) Patent No.: US 12,558,403 B2
(45) Date of Patent: Feb. 24, 2026

(54) ANTI-TUMOR FUSION PROTEIN, PREPARATION METHOD THEREFOR AND APPLICATION THEREOF

(71) Applicant: GUANGDONG TAIHE MEDICINE SCIENCE & TECHNOLOGY CO., LTD, Guangdong (CN)

(72) Inventors: Yingqi Zhang, Shaanxi (CN); Fulin Fan, Guangdong (CN)

(73) Assignee: GUANGDONG TAIHE MEDICINE SCIENCE & TECHNOLOGY CO., LTD, Guangdong (CN)

( * ) Notice: Subject to any disclaimer, the term of this patent is extended or adjusted under 35 U.S.C. 154(b) by 690 days.

(21) Appl. No.: 17/758,676

(22) PCT Filed: Jan. 12, 2021

(86) PCT No.: PCT/CN2021/071335
§ 371 (c)(1),
(2) Date: Jul. 12, 2022

(87) PCT Pub. No.: WO2021/143695
PCT Pub. Date: Jul. 22, 2021

(65) Prior Publication Data
US 2023/0226157 A1     Jul. 20, 2023

(30) Foreign Application Priority Data

Jan. 13, 2020    (CN) .......................... 202010033954.8

(51) Int. Cl.
| | |
|---|---|
| *A61K 38/46* | (2006.01) |
| *C07K 14/47* | (2006.01) |
| *C12N 9/16* | (2006.01) |

(52) U.S. Cl.
CPC ............ *A61K 38/465* (2013.01); *C07K 14/47* (2013.01); *C12N 9/16* (2013.01); *C07K 2319/00* (2013.01); *C12Y 301/03048* (2013.01)

(58) Field of Classification Search
CPC .. A61K 38/465; C07K 14/47; C07K 2319/00; C12N 9/16; C12Y 301/03048
See application file for complete search history.

(56) References Cited

U.S. PATENT DOCUMENTS

| | | | | |
|---|---|---|---|---|
| 2004/0105871 A1 * | 6/2004 | Robinson | ............... | C12N 15/67 |
| | | | | 435/235.1 |
| 2021/0254037 A1 * | 8/2021 | Shin | ........................ | A61P 27/02 |
| 2023/0192769 A1 * | 6/2023 | Zhou | ........................ | A61P 31/14 |
| | | | | 514/3.7 |

FOREIGN PATENT DOCUMENTS

| | | |
|---|---|---|
| CN | 106852146 A | 6/2017 |
| CN | 109553660 A | 4/2019 |

| | | | | |
|---|---|---|---|---|
| JP | 2019535292 A | 12/2019 | | |
| WO | 2011140365 A1 | 11/2011 | | |
| WO | 2016168702 A1 | 10/2016 | | |
| WO | 2017079723 A1 | 5/2017 | | |
| WO | WO-2020076723 A1 * | 4/2020 | ......... | G01N 33/5748 |

OTHER PUBLICATIONS

Saito Y, Furukawa T, Arano Y, Fujibayashi Y, Saga T. Fusion protein based on Grb2-SH2 domain for cancer therapy. Biochem Biophys Res Commun. Aug. 20, 2010;399(2):262-7. doi: 10.1016/j.bbrc. 2010.07.066. Epub Jul. 21, 2010. PMID: 20655296. (Year: 2010).*
Demarco, 2022 (Squamous cell carcinomas: 8 thinks to know about the 'cancer of surfaces') https://www.mdanderson.org/cancerwise/ squamous-cell-carcinomas--8-things-to-know-about-the--cancer-of-the-surfaces.h00-159544479.html (Year: 2022).*
George RA, Heringa J. An analysis of protein domain linkers: their classification and role in protein folding. Protein Eng. Nov. 2002; 15(11):871-9. doi: 10.1093/protein/15.11.871. PMID: 12538906. (Year: 2003).*
Sharma A, Tandon M, Bangari DS, Mittal SK. Adenoviral vector-based strategies for cancer therapy. Curr Drug ther. May 1, 2009;4(2):117-138. doi: 10.2174/157488509788185123. PMID: 20160875; PMCID: PMC2771947. (Year: 2009).*
Tojjari et al., Overcoming Immune Checkpoint Therapy Resistance with SHP2 Inhibition in Cancer and Immune Cells: A Review of the Literature and Novel Combinatorial Approaches. Cancers (Basel). Nov. 13, 2023;15(22):5384. doi: 10.3390/cancers15225384. PMID: 38001644; PMCID: PMC10670368. (Year: 2023).*
International Search Report and Written Opinion issued in PCT/ CN2021/071335, dated Apr. 9, 2021, 17 pages provided, (with English translation).
Dempke, W.C.M. et al., "Targeting SHP1, 2 and SHIP Pathways: A Novel Strategy for Cancer Treatment", Oncology, Jun. 20, 2018, pp. 257-269, cited in ISR.
Shi et al., "Tum or targeting carrier equipped with cell-penetrating peptides", Chin J Cancer Biother, Feb. 2010, vol. 17, No. 1, www. biother.org, 6 pages, cited in ISR; with English Abstract.
International Preliminary Report on Patentability issued in PCT/ CN2021/071335, dated Jul. 19, 2022, with English translation, 4 pages provided.
The extended European Search Report issued in European Application No. 21741405.1, dated Dec. 15, 2023.
Dunican et al., "Designing cell-permeant phosphopeptides to modulate intracellular signaling pathways", Biopolymers (Peptide Science), vol. 60, pp. 45-60, 2001.
Liu et al., "(Arg)9-SH2 superbinder: a novel promising anticancer therapy to melanoma by blocking phosphotyrosine signaling", J Exp Clin Cancer Res., Published online Jul. 5, 2018.
Office Action issued in Japanese Application No. 2022-0543131, dated Nov. 22, 2024, with English machine translation.

(Continued)

*Primary Examiner* — Louise W Humphrey
*Assistant Examiner* — Rachel Emily Martin
(74) *Attorney, Agent, or Firm* — HSML P.C.

(57) ABSTRACT

Provided are an anti-tumor fusion protein, a preparation method therefor and an application thereof. Specifically, the fusion protein contacts a CPP element, an optional linking element, and a SH2 domain of SHP2 or SHP1 or an active fragment thereof. The obtained fusion protein has an extremely excellent anti-tumor effect.

11 Claims, 12 Drawing Sheets

Specification includes a Sequence Listing.

(56)                References Cited

OTHER PUBLICATIONS

Yin et al., "A recombined fusion protein PTD-Grb2-SH2 inhibits the proliferation of breast cancer cells in vitro", International Journal of Oncology 42: 1061-1069, 2013. Cited in Japanese Office Action.

Katterle et al., "Antitumour effects of PLC-g1-(SH2)2-TAT fusion proteins on EGFR/c-erbB-2-positive breast cancer cells", British Journal of Cancer (2004) 90, 230-235. Cited in Japanese Office Action.

* cited by examiner

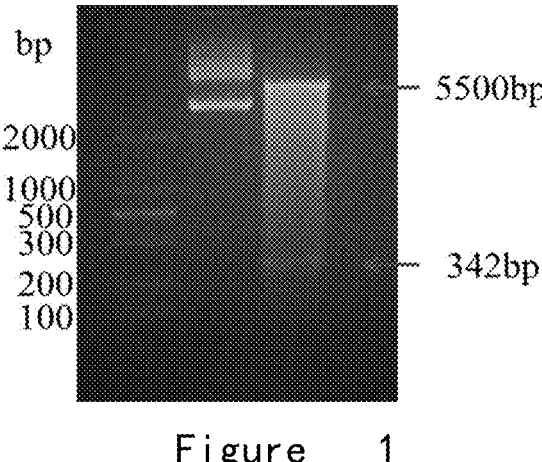
Figure    1
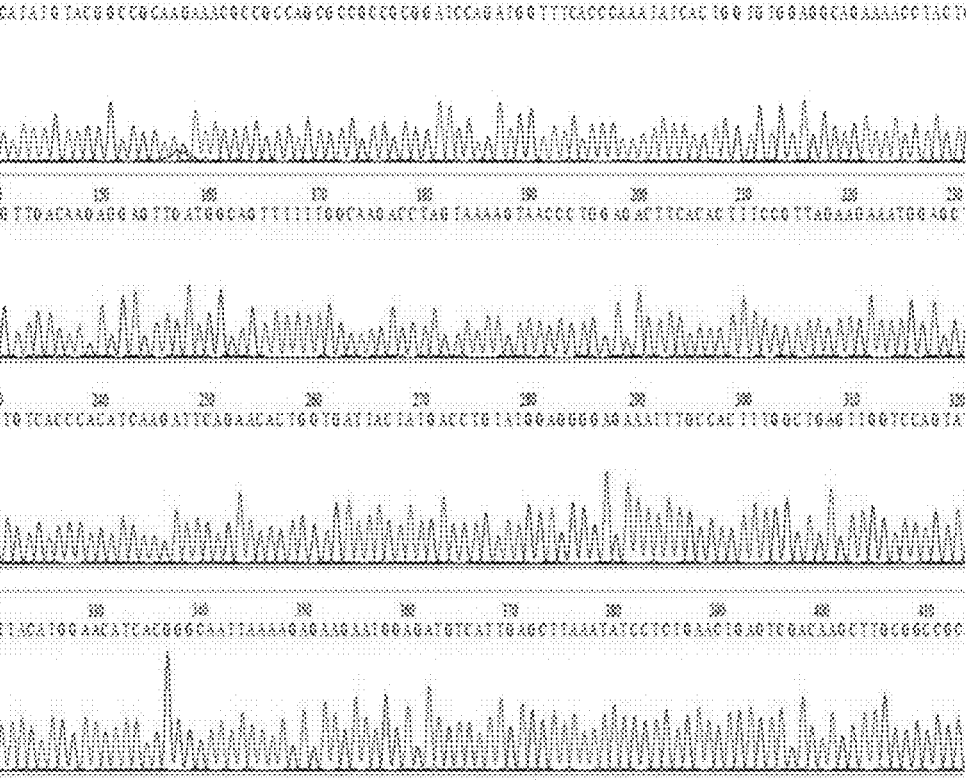
Figure    2

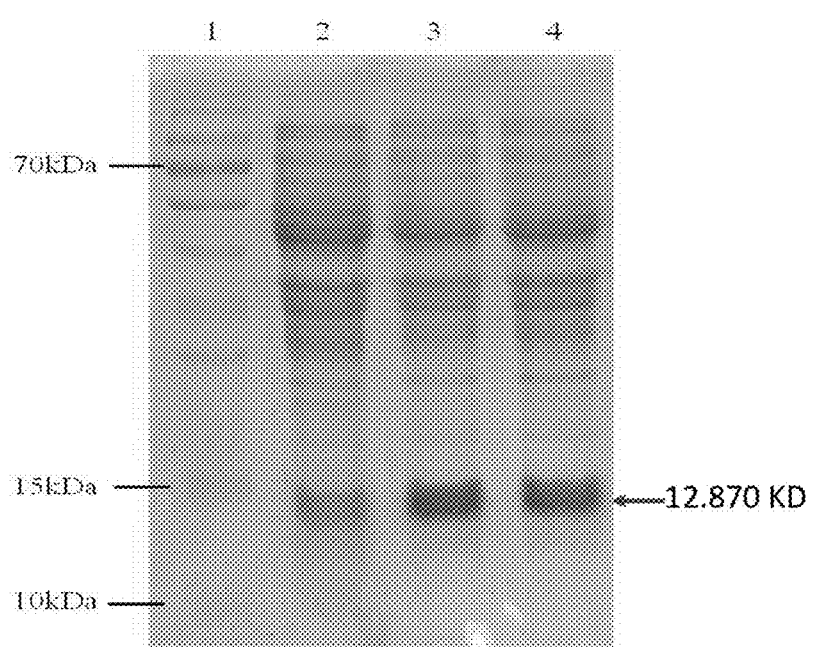
Figure    3
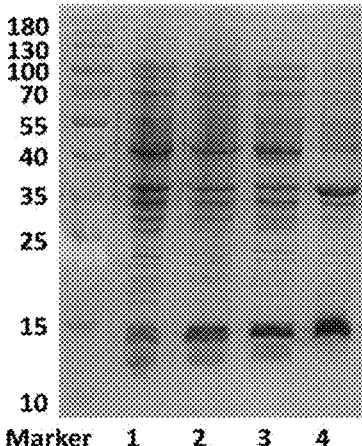
Figure    4
Figure    5

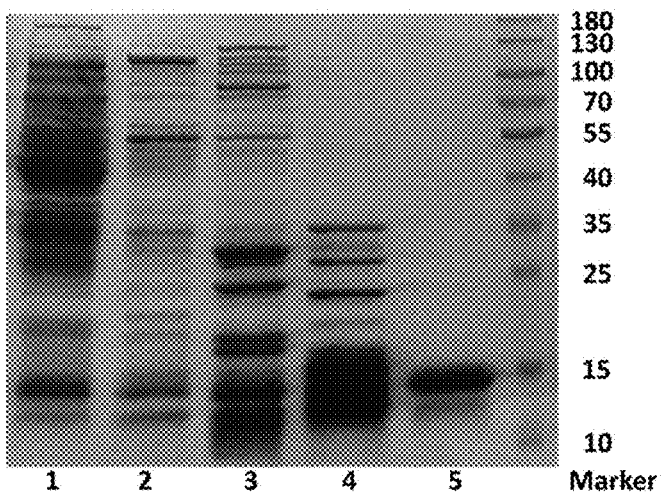
Figure 6
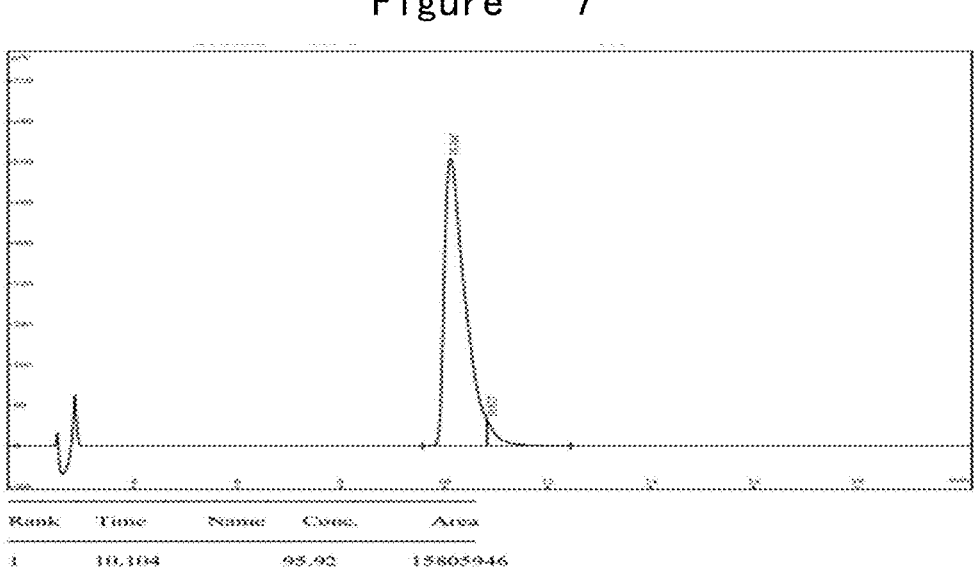
Figure 7
Figure 8

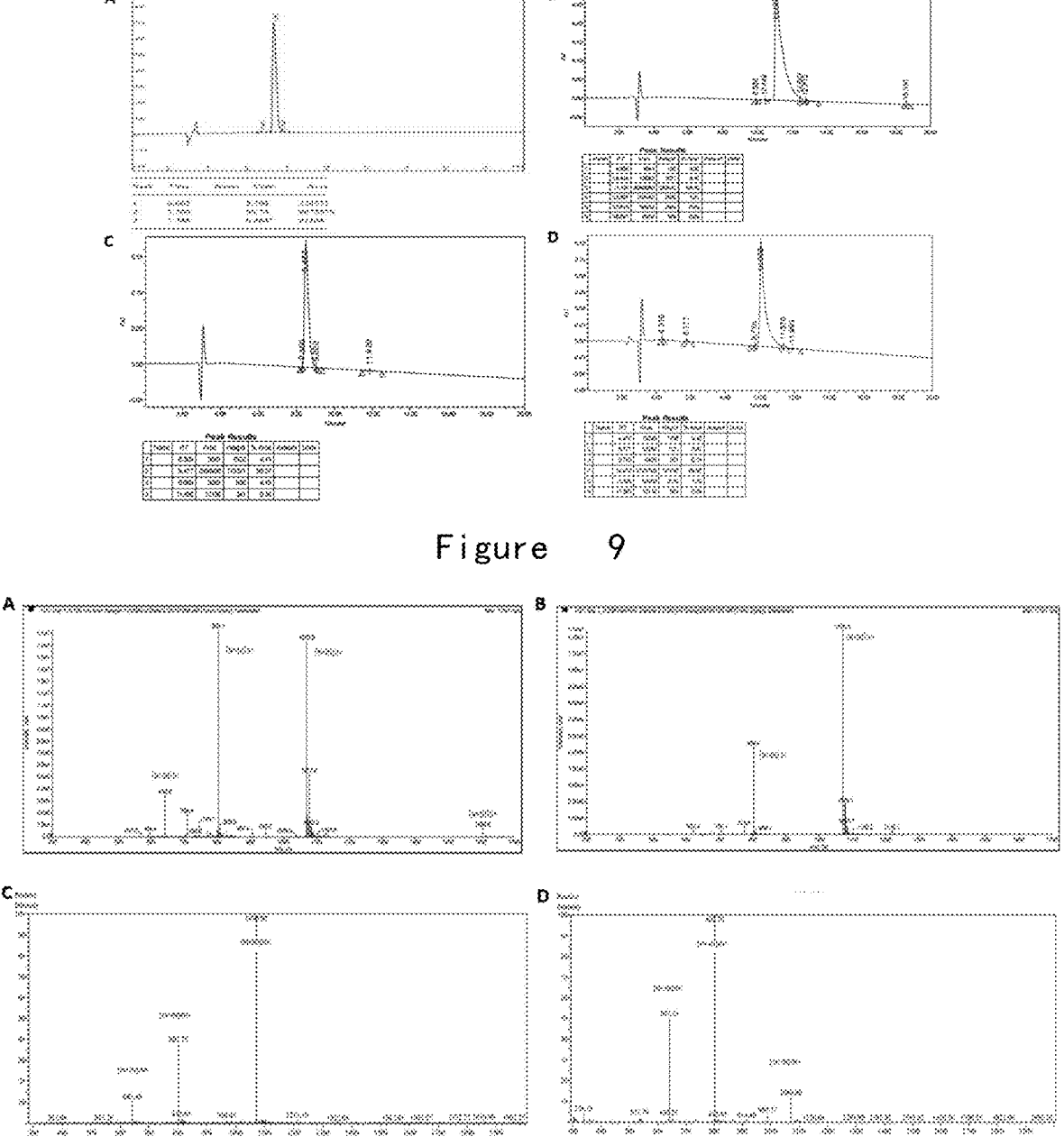
Figure    9
Figure    10

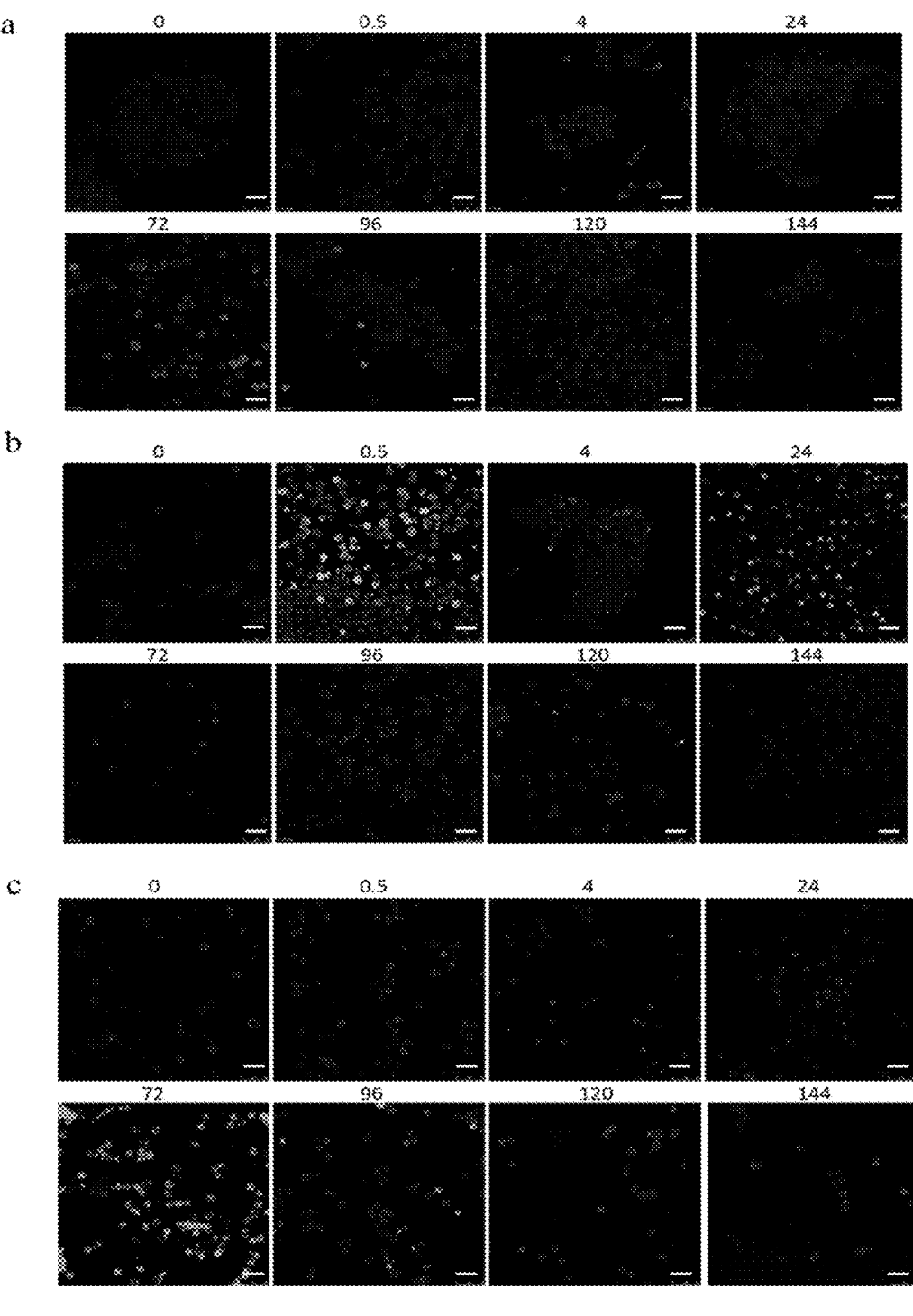
Figure    11

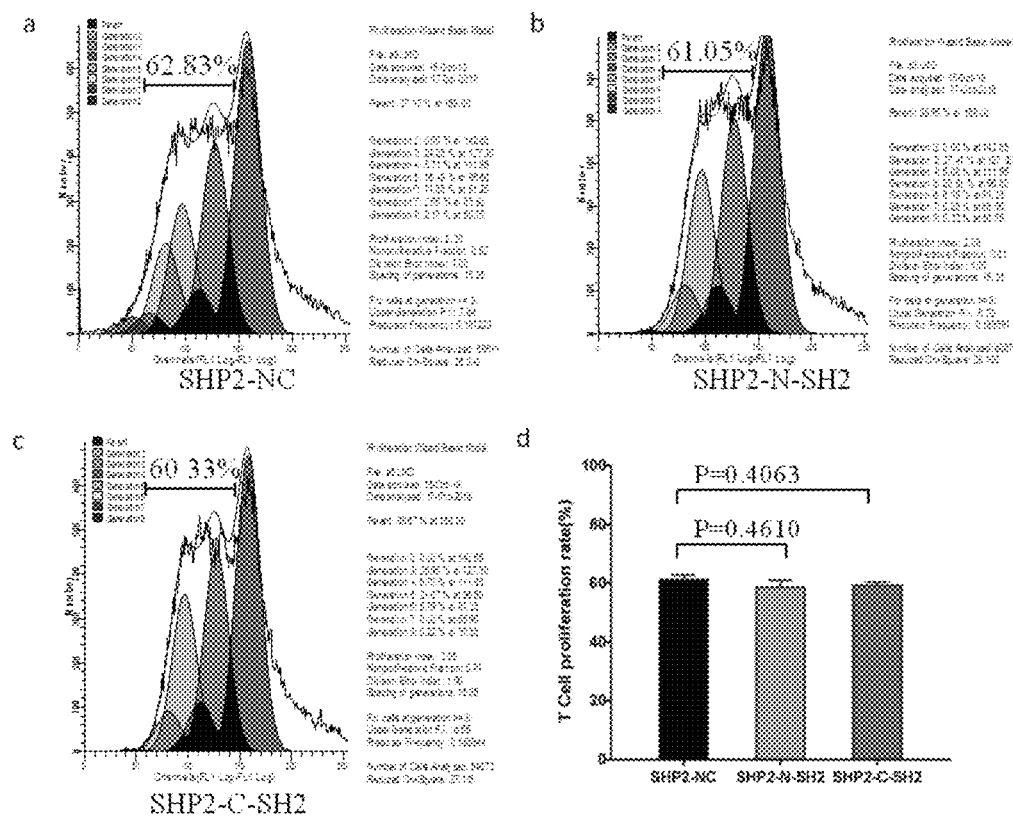
Figure     12
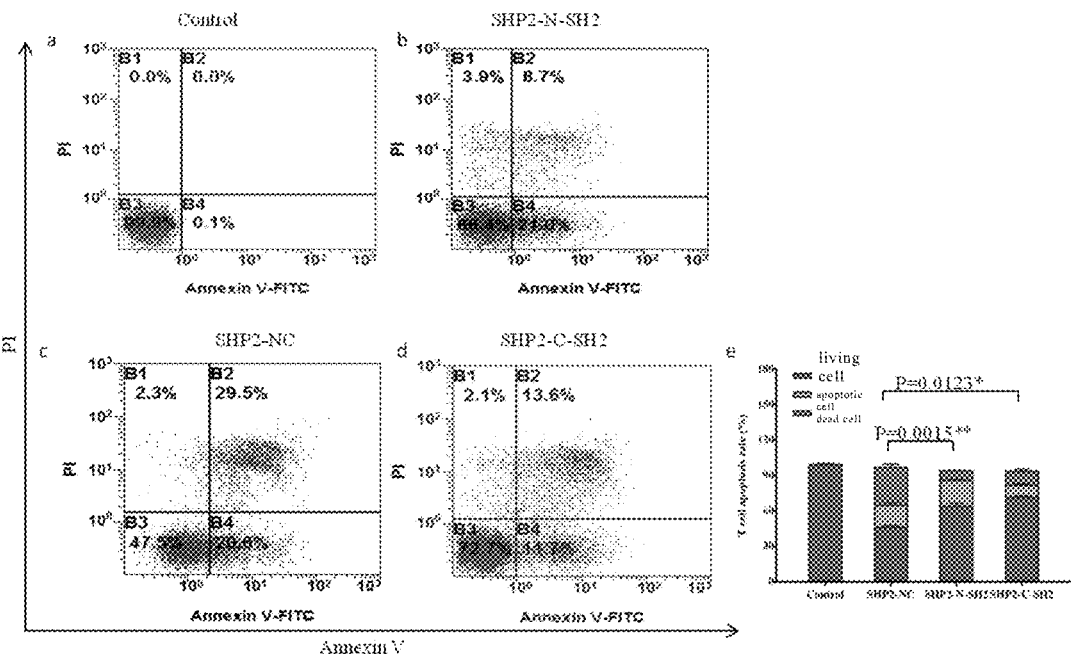
Figure     13

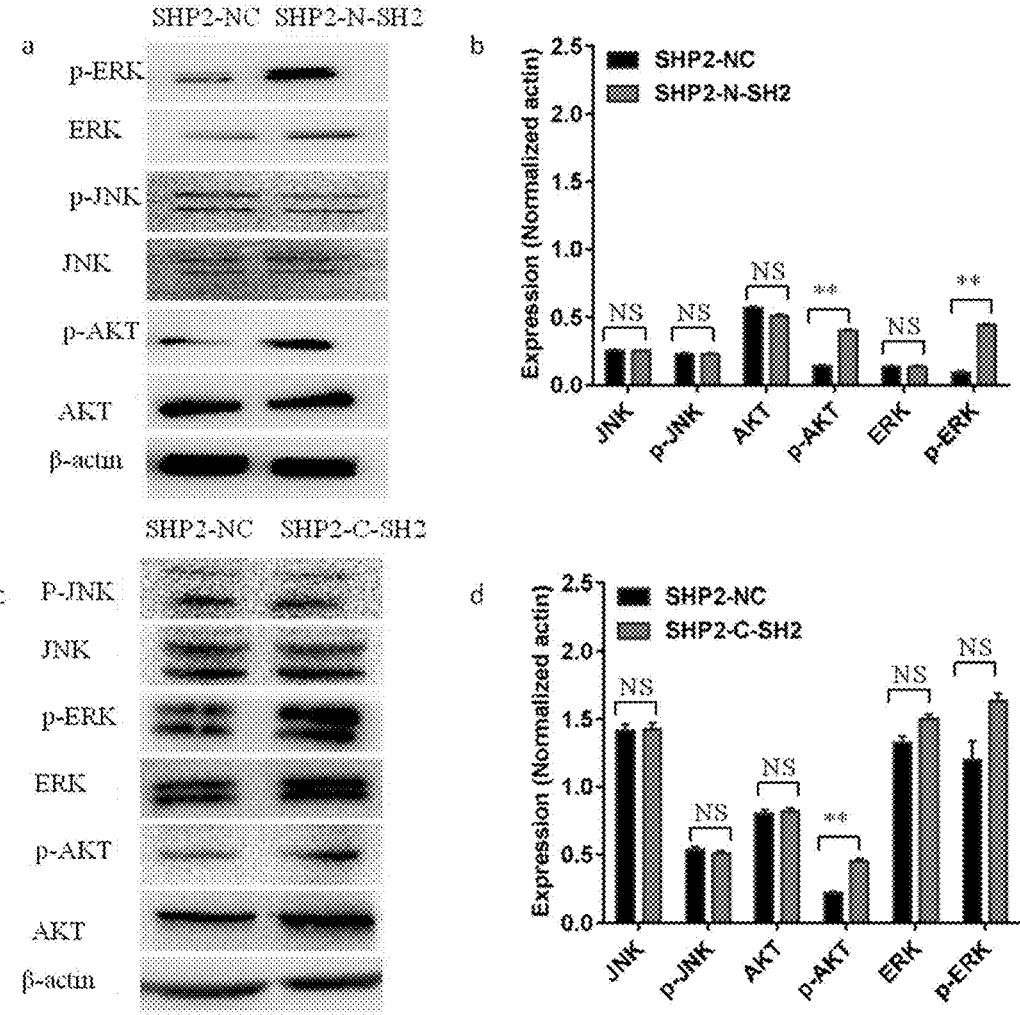
Figure    14
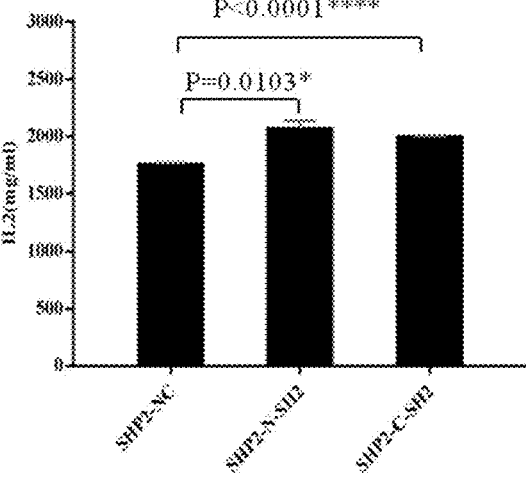
Figure    15

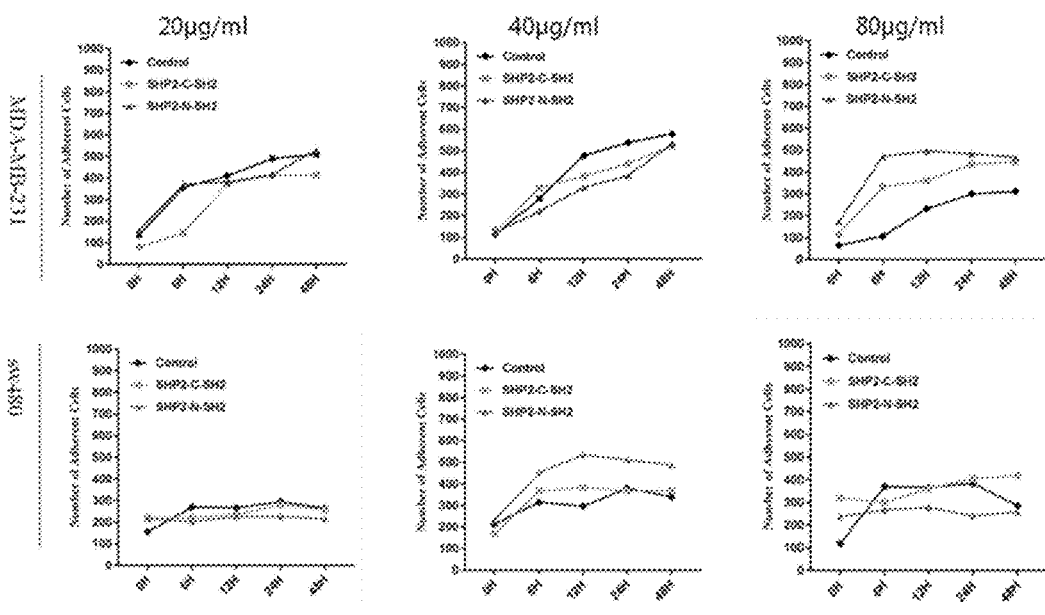
Figure    16
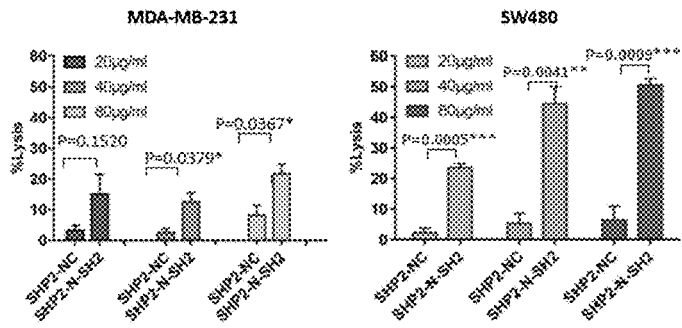
Figure    17
Figure    18

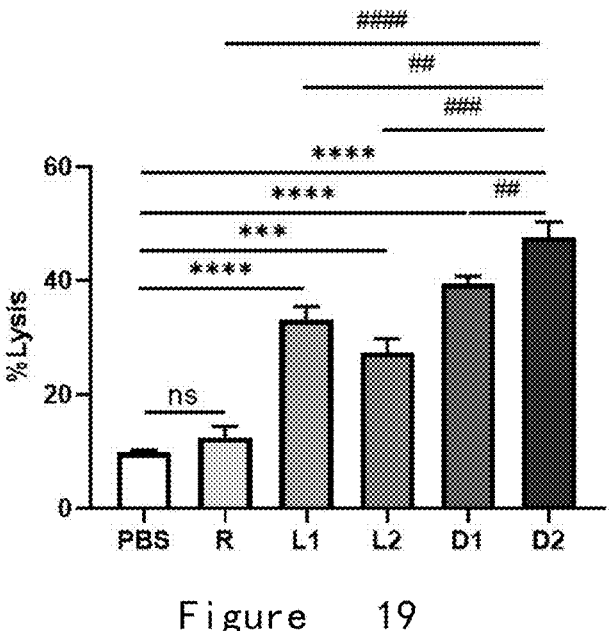
Figure    19
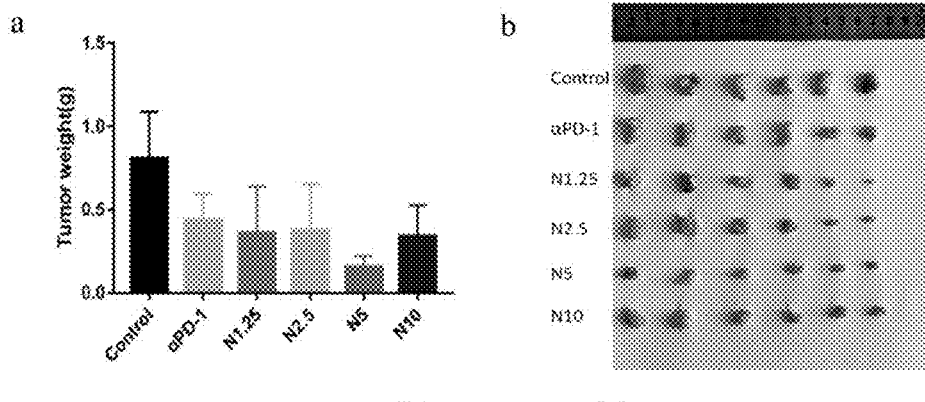
Figure    20
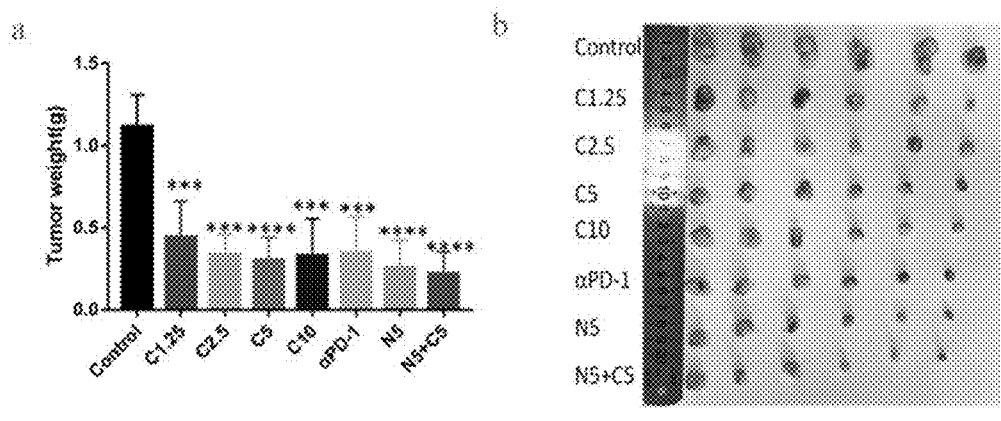
Figure    21

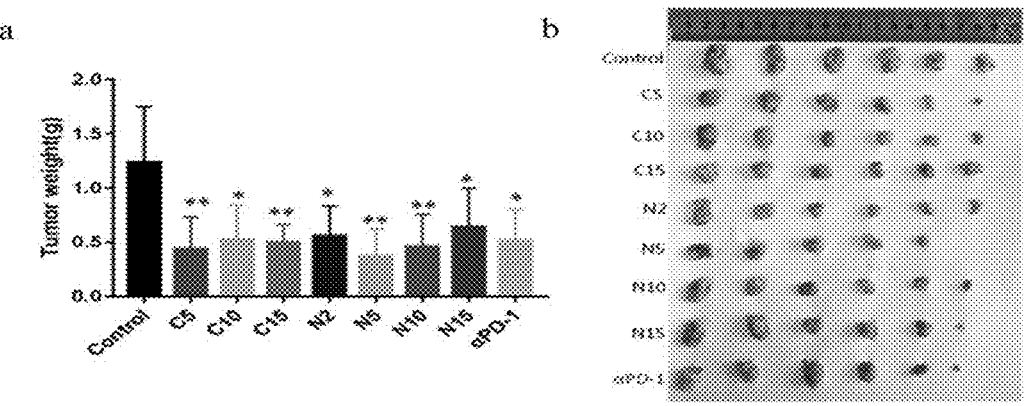
Figure     22
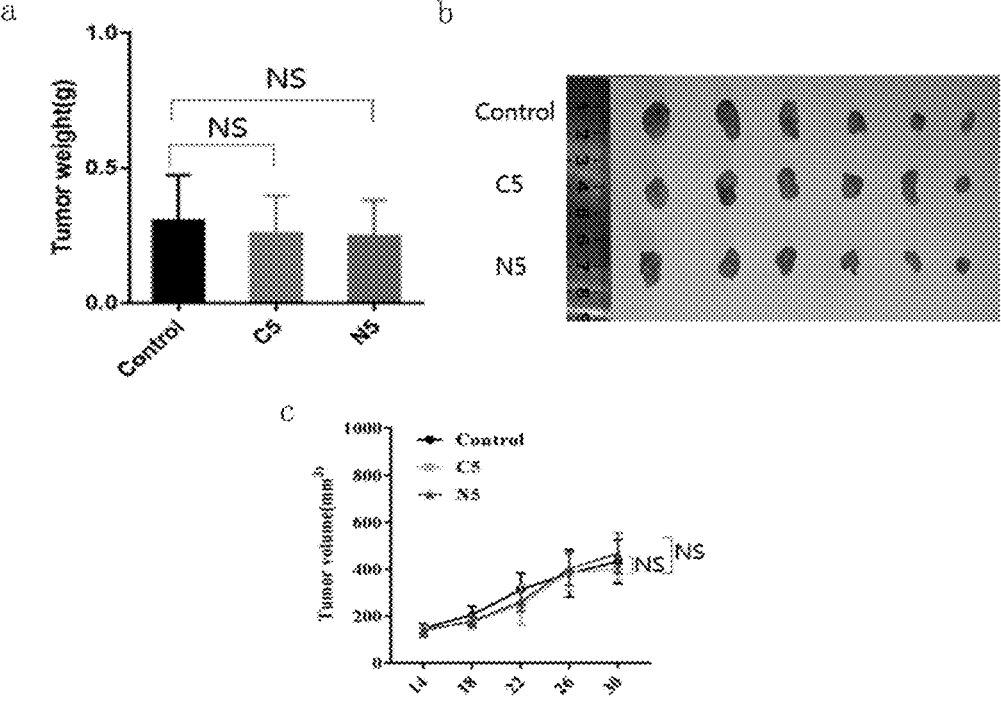
Figure     23

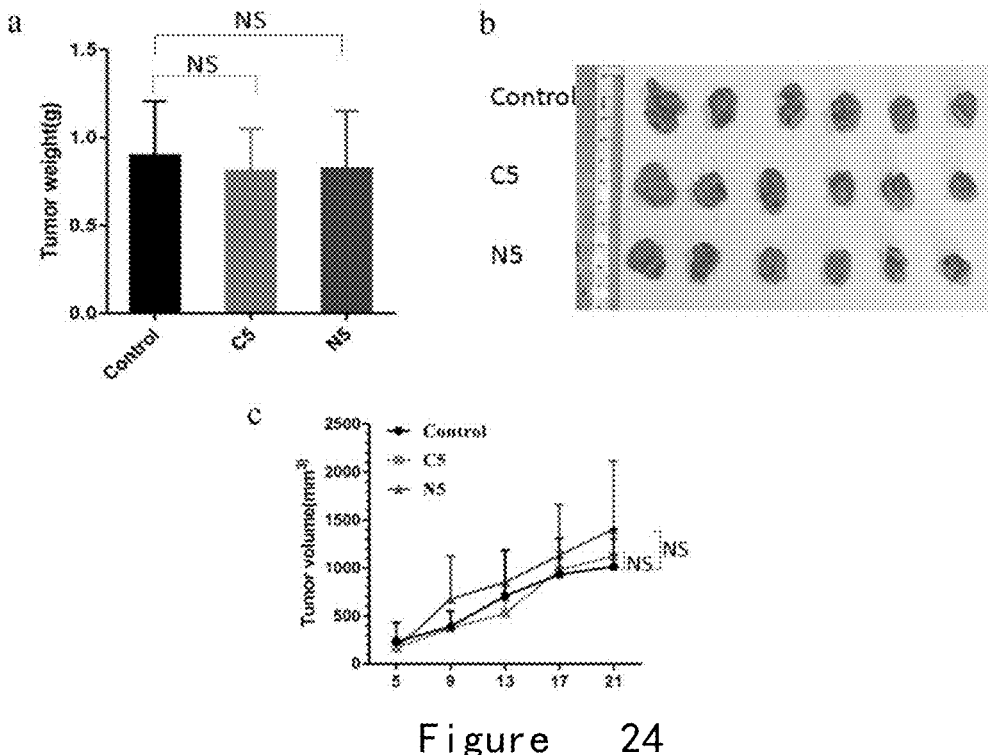
Figure    24
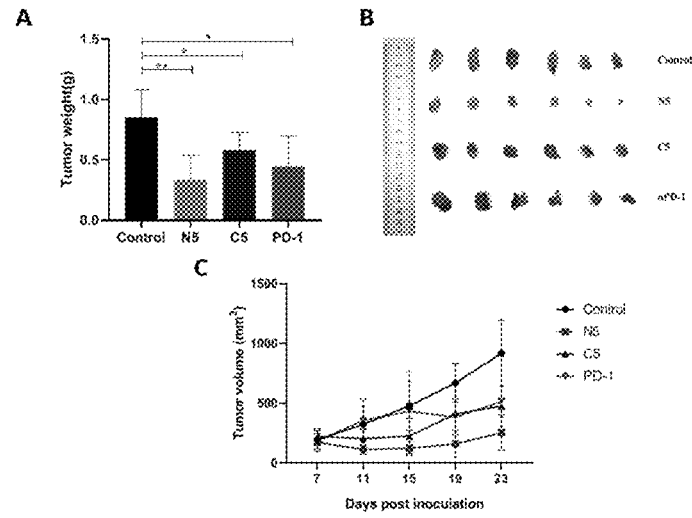
Figure    25

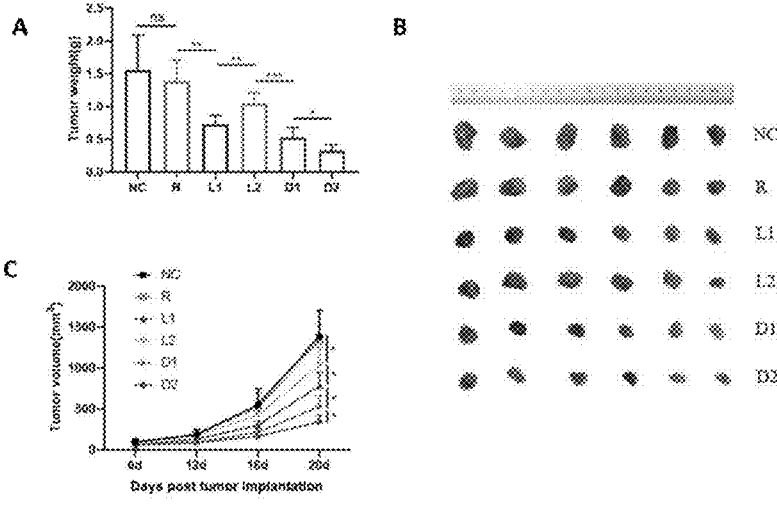
Figure    26

SEQUENCE LISTING

<160> NUMBER OF SEQ ID NOS: 21

<210> SEQ ID NO 1
<211> LENGTH: 11
<212> TYPE: PRT
<213> ORGANISM: Homo sapiens

<400> SEQUENCE: 1

Tyr Gly Arg Lys Lys Arg Arg Gln Arg Arg Arg
1               5                   10

<210> SEQ ID NO 2
<211> LENGTH: 99
<212> TYPE: PRT
<213> ORGANISM: Homo sapiens

<400> SEQUENCE: 2

Arg Trp Phe His Pro Asn Ile Thr Gly Val Glu Ala Glu Asn Leu Leu
1               5                   10                  15

Leu Thr Arg Gly Val Asp Gly Ser Phe Leu Ala Arg Pro Ser Lys Ser
            20                  25                  30

Asn Pro Gly Asp Phe Thr Leu Ser Val Arg Arg Asn Gly Ala Val Thr
        35                  40                  45

His Ile Lys Ile Gln Asn Thr Gly Asp Tyr Tyr Asp Leu Tyr Gly Gly
    50                  55                  60

Glu Lys Phe Ala Thr Leu Ala Glu Leu Val Gln Tyr Tyr Met Glu His
65                  70                  75                  80

His Gly Gln Leu Lys Glu Lys Asn Gly Asp Val Ile Glu Leu Lys Tyr
                85                  90                  95

Pro Leu Asn

-continued

```
<210> SEQ ID NO 3
<211> LENGTH: 108
<212> TYPE: PRT
<213> ORGANISM: Homo sapiens

<400> SEQUENCE: 3

Arg Trp Phe His Gly His Leu Ser Gly Lys Glu Ala Glu Lys Leu Leu
1               5                   10                  15

Thr Glu Lys Gly Lys His Gly Ser Phe Leu Val Arg Glu Ser Gln Ser
            20                  25                  30

His Pro Gly Asp Phe Val Leu Ser Val Arg Thr Gly Asp Asp Lys Gly
        35                  40                  45

Glu Ser Asn Asp Gly Lys Ser Lys Val Thr His Val Met Ile Arg Cys
    50                  55                  60

Gln Glu Leu Lys Tyr Asp Val Gly Gly Gly Glu Arg Phe Asp Ser Leu
65                  70                  75                  80

Thr Asp Leu Val Glu His Tyr Lys Lys Asn Pro Met Val Glu Thr Leu
                85                  90                  95

Gly Thr Val Leu Gln Leu Lys Gln Pro Leu Asn Thr
            100                 105

<210> SEQ ID NO 4
<211> LENGTH: 112
<212> TYPE: PRT
<213> ORGANISM: artificial sequence
<220> FEATURE:
<223> OTHER INFORMATION: the fusion protein

<400> SEQUENCE: 4

Tyr Gly Arg Lys Lys Arg Arg Gln Arg Arg Gly Ser Arg Trp Phe
1               5                   10                  15

His Pro Asn Ile Thr Gly Val Glu Ala Glu Asn Leu Leu Leu Thr Arg
            20                  25                  30

Gly Val Asp Gly Ser Phe Leu Ala Arg Pro Ser Lys Ser Asn Pro Gly
        35                  40                  45

Asp Phe Thr Leu Ser Val Arg Arg Asn Gly Ala Val Thr His Ile Lys
    50                  55                  60

Ile Gln Asn Thr Gly Asp Tyr Tyr Asp Leu Tyr Gly Gly Glu Lys Phe
65                  70                  75                  80

Ala Thr Leu Ala Glu Leu Val Gln Tyr Tyr Met Glu His His Gly Gln
                85                  90                  95

Leu Lys Glu Lys Asn Gly Asp Val Ile Glu Leu Lys Tyr Pro Leu Asn
            100                 105                 110

<210> SEQ ID NO 5
<211> LENGTH: 26
<212> TYPE: PRT
<213> ORGANISM: artificial sequence
<220> FEATURE:
<223> OTHER INFORMATION: the fusion protein

<400> SEQUENCE: 5

Tyr Gly Arg Lys Lys Arg Arg Gln Arg Arg Pro Pro Val Arg Glu
1               5                   10                  15

Ser Gln Ser His Pro Gly Asp Phe Val Leu
            20                  25

<210> SEQ ID NO 6
```

```
<211> LENGTH: 26
<212> TYPE: PRT
<213> ORGANISM: artificial sequence
<220> FEATURE:
<223> OTHER INFORMATION: the fusion protein

<400> SEQUENCE: 6

Leu Val Phe Asp Gly Pro His Ser Gln Ser Glu Arg Val Pro Pro Arg
1               5                   10                  15

Arg Arg Gln Arg Arg Lys Lys Arg Gly Tyr
            20                  25

<210> SEQ ID NO 7
<211> LENGTH: 26
<212> TYPE: PRT
<213> ORGANISM: artificial sequence
<220> FEATURE:
<223> OTHER INFORMATION: the fusion protein

<400> SEQUENCE: 7

Tyr Gly Arg Lys Lys Arg Arg Gln Arg Arg Pro Pro Val Arg Glu
1               5                   10                  15

Ser Gln Ser His Pro Gly Asp Phe Val Leu
            20                  25

<210> SEQ ID NO 8
<211> LENGTH: 26
<212> TYPE: PRT
<213> ORGANISM: artificial sequence
<220> FEATURE:
<223> OTHER INFORMATION: the fusion protein

<400> SEQUENCE: 8

Leu Val Phe Asp Gly Pro His Ser Gln Ser Glu Arg Val Pro Pro Arg
1               5                   10                  15

Arg Arg Gln Arg Arg Lys Lys Arg Gly Tyr
            20                  25

<210> SEQ ID NO 9
<211> LENGTH: 351
<212> TYPE: DNA
<213> ORGANISM: artificial sequence
<220> FEATURE:
<223> OTHER INFORMATION: nucleotide sequence of TAT-N-SH2 gene

<400> SEQUENCE: 9
catatgtacg gccgcaagaa acgccgccag cgccgccgcg gatccagatg gtttcaccca      60
aatatcactg gtgtggaggc agaaaaccta ctgttgacaa gaggagttga tggcagtttt     120
ttggcaagac ctagtaaaag taaccctgga gacttcacac tttccgttag aagaaatgga     180
gctgtcaccc acatcaagat tcagaacact ggtgattact atgacctgta tggaggggag     240
aaatttgcca ctttggctga gttggtccag tattacatgg aacatcacgg gcaattaaaa     300
gagaagaatg agatgtcat tgagcttaaa tatcctctga actgagtcga c              351

<210> SEQ ID NO 10
<211> LENGTH: 7
<212> TYPE: PRT
<213> ORGANISM: artificial sequence
<220> FEATURE:
<223> OTHER INFORMATION: nucleotide sequence of TAT-N-SH2 gene

<400> SEQUENCE: 10

Cys Ala Asp Pro Thr Ser Glu
```

-continued

```
1               5

<210> SEQ ID NO 11
<211> LENGTH: 214
<212> TYPE: PRT
<213> ORGANISM: artificial sequence
<220> FEATURE:
<223> OTHER INFORMATION: Z2

<400> SEQUENCE: 11

Arg Trp Phe His Pro Asn Ile Thr Gly Val Glu Ala Glu Asn Leu Leu
1               5                   10                  15

Leu Thr Arg Gly Val Asp Gly Ser Phe Leu Ala Arg Pro Ser Lys Ser
            20                  25                  30

Asn Pro Gly Asp Phe Thr Leu Ser Val Arg Arg Asn Gly Ala Val Thr
            35                  40                  45

His Ile Lys Ile Gln Asn Thr Gly Asp Tyr Tyr Asp Leu Tyr Gly Gly
        50                  55                  60

Glu Lys Phe Ala Thr Leu Ala Glu Leu Val Gln Tyr Tyr Met Glu His
65                  70                  75                  80

His Gly Gln Leu Lys Glu Lys Asn Gly Asp Val Ile Glu Leu Lys Tyr
                85                  90                  95

Pro Leu Asn Cys Ala Asp Pro Thr Ser Glu Arg Trp Phe His Gly His
            100                 105                 110

Leu Ser Gly Lys Glu Ala Glu Lys Leu Leu Thr Glu Lys Gly Lys His
            115                 120                 125

Gly Ser Phe Leu Val Arg Glu Ser Gln Ser His Pro Gly Asp Phe Val
        130                 135                 140

Leu Ser Val Arg Thr Gly Asp Asp Lys Gly Glu Ser Asn Asp Gly Lys
145                 150                 155                 160

Ser Lys Val Thr His Val Met Ile Arg Cys Gln Glu Leu Lys Tyr Asp
                165                 170                 175

Val Gly Gly Gly Glu Arg Phe Asp Ser Leu Thr Asp Leu Val Glu His
            180                 185                 190

Tyr Lys Lys Asn Pro Met Val Glu Thr Leu Gly Thr Val Leu Gln Leu
            195                 200                 205

Lys Gln Pro Leu Asn Thr
    210

<210> SEQ ID NO 12
<211> LENGTH: 99
<212> TYPE: PRT
<213> ORGANISM: Homo sapiens

<400> SEQUENCE: 12

Arg Trp Phe His Arg Asp Leu Ser Gly Leu Asp Ala Glu Thr Leu Leu
1               5                   10                  15

Lys Gly Arg Gly Val His Gly Ser Phe Leu Ala Arg Pro Ser Arg Lys
            20                  25                  30

Asn Gln Gly Asp Phe Ser Leu Ser Val Arg Val Gly Asp Gln Val Thr
            35                  40                  45

His Ile Arg Ile Gln Asn Ser Gly Asp Phe Tyr Asp Leu Tyr Gly Gly
        50                  55                  60

Glu Lys Phe Ala Thr Leu Thr Glu Leu Val Glu Tyr Tyr Thr Gln Gln
65                  70                  75                  80

Gln Gly Val Leu Gln Asp Arg Asp Gly Thr Ile Ile His Leu Lys Tyr
                85                  90                  95
```

```
Pro Leu Asn

<210> SEQ ID NO 13
<211> LENGTH: 107
<212> TYPE: PRT
<213> ORGANISM: Homo sapiens

<400> SEQUENCE: 13

Arg Trp Tyr His Gly His Met Ser Gly Gly Gln Ala Glu Thr Leu Leu
1               5                   10                  15

Gln Ala Lys Gly Glu Pro Trp Thr Phe Leu Val Arg Glu Ser Leu Ser
            20                  25                  30

Gln Pro Gly Asp Phe Val Leu Ser Val Leu Ser Asp Gln Pro Lys Ala
        35                  40                  45

Gly Pro Gly Ser Pro Leu Arg Val Thr His Ile Lys Val Met Cys Glu
    50                  55                  60

Gly Gly Arg Tyr Thr Val Gly Gly Leu Glu Thr Phe Asp Ser Leu Thr
65                  70                  75                  80

Asp Leu Val Glu His Phe Lys Lys Thr Gly Ile Glu Glu Ala Ser Gly
                85                  90                  95

Ala Phe Val Tyr Leu Arg Gln Pro Tyr Tyr Ala
            100                 105

<210> SEQ ID NO 14
<211> LENGTH: 213
<212> TYPE: PRT
<213> ORGANISM: artificial sequence
<220> FEATURE:
<223> OTHER INFORMATION: Z2

<400> SEQUENCE: 14

Arg Trp Phe His Arg Asp Leu Ser Gly Leu Asp Ala Glu Thr Leu Leu
1               5                   10                  15

Lys Gly Arg Gly Val His Gly Ser Phe Leu Ala Arg Pro Ser Arg Lys
            20                  25                  30

Asn Gln Gly Asp Phe Ser Leu Ser Val Arg Val Gly Asp Gln Val Thr
        35                  40                  45

His Ile Arg Ile Gln Asn Ser Gly Asp Phe Tyr Asp Leu Tyr Gly Gly
    50                  55                  60

Glu Lys Phe Ala Thr Leu Thr Glu Leu Val Glu Tyr Tyr Thr Gln Gln
65                  70                  75                  80

Gln Gly Val Leu Gln Asp Arg Asp Gly Thr Ile Ile His Leu Lys Tyr
                85                  90                  95

Pro Leu Asn Cys Ser Asp Pro Thr Ser Glu Arg Trp Tyr His Gly His
            100                 105                 110

Met Ser Gly Gly Gln Ala Glu Thr Leu Leu Gln Ala Lys Gly Glu Pro
        115                 120                 125

Trp Thr Phe Leu Val Arg Glu Ser Leu Ser Gln Pro Gly Asp Phe Val
    130                 135                 140

Leu Ser Val Leu Ser Asp Gln Pro Lys Ala Gly Pro Gly Ser Pro Leu
145                 150                 155                 160

Arg Val Thr His Ile Lys Val Met Cys Glu Gly Gly Arg Tyr Thr Val
                165                 170                 175

Gly Gly Leu Glu Thr Phe Asp Ser Leu Thr Asp Leu Val Glu His Phe
            180                 185                 190

Lys Lys Thr Gly Ile Glu Glu Ala Ser Gly Ala Phe Val Tyr Leu Arg
```

-continued

```
              195                200                205

Gln Pro Tyr Tyr Ala
    210

<210> SEQ ID NO 15
<211> LENGTH: 27
<212> TYPE: PRT
<213> ORGANISM: Homo sapiens

<400> SEQUENCE: 15

Gly Leu Ala Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 16
<211> LENGTH: 20
<212> TYPE: PRT
<213> ORGANISM: Homo sapiens

<400> SEQUENCE: 16

Gly Leu Trp Arg Ala Leu Trp Arg Leu Leu Arg Ser Leu Trp Arg Leu
1               5                   10                  15

Leu Trp Lys Ala
            20

<210> SEQ ID NO 17
<211> LENGTH: 18
<212> TYPE: PRT
<213> ORGANISM: Homo sapiens

<400> SEQUENCE: 17

Leu Leu Ile Ile Leu Arg Arg Arg Ile Arg Lys Gln Ala His Ala His
1               5                   10                  15

Ser Lys

<210> SEQ ID NO 18
<211> LENGTH: 16
<212> TYPE: PRT
<213> ORGANISM: Homo sapiens

<400> SEQUENCE: 18

Arg Gln Ile Lys Ile Trp Phe Gln Asn Arg Arg Met Lys Trp Lys Lys
1               5                   10                  15

<210> SEQ ID NO 19
<211> LENGTH: 12
<212> TYPE: PRT
<213> ORGANISM: Homo sapiens

<400> SEQUENCE: 19

Ala Ala Val Leu Leu Pro Val Leu Leu Ala Ala Pro
1               5                   10

<210> SEQ ID NO 20
<211> LENGTH: 33
<212> TYPE: PRT
<213> ORGANISM: Homo sapiens

<400> SEQUENCE: 20

Asp Ala Ala Thr Ala Thr Arg Gly Arg Ser Ala Ala Ser Arg Pro Thr
1               5                   10                  15
```

```
Glu Arg Pro Arg Ala Pro Ala Arg Ser Ala Ser Arg Pro Arg Arg Val
            20                  25                  30

Asp

<210> SEQ ID NO 21
<211> LENGTH: 14
<212> TYPE: PRT
<213> ORGANISM: Homo sapiens

<400> SEQUENCE: 21

Arg Arg Arg Arg Arg Arg Arg Arg Arg Arg Arg Arg Arg Arg
1               5                   10
```

ANTI-TUMOR FUSION PROTEIN, PREPARATION METHOD THEREFOR AND APPLICATION THEREOF

TECHNICAL FIELD

The present invention relates to the fields of biology and medicine, and more particularly to an anti-tumor fusion protein and its preparation method and application.

SEQUENCE LISTING

The present application is being filed along with a Sequence Listing in txt. Format. The Sequence Listing is provided as a file entitled sequence_listing.txt, created on Mar. 9, 2023, which is 12.8 kb in size. The information in the txt. format of Sequence Listing is incorporated herein by reference in its entirety.

BACKGROUND

Immune checkpoint blocking agent has become an important target of tumor immunotherapy. Immune checkpoint blocking therapy targeting PD-1/PD-L1 is to use the body's own immune system to resist and fight against malignant tumors, a new generation of anticancer immunotherapies that substantially improve patient overall survival. However, several studies have reported that only a minority of 20% to 30% of patients respond to the blocking agent, and some patients develop drug resistance after receiving drug treatment. In the case of low response rate of monotherapy, the development of new immune checkpoint blocking drugs and the combination strategy of different immune checkpoint drugs have become new ways to improve the response rate of patients. However, the problems of low clinical response rate and drug resistance cannot be completely solved, and the combined application of multiple therapies has problems such as joint timing, dose optimization, and pharmacoeconomics. Therefore, designing a universal immune checkpoint blocking agent (Universal immune check point blockade, UICB) targeting the common targets of different immune checkpoints may be a key breakthrough for the above problems.

Therefore, there is an urgent need in the art to develop more effective anti-tumor fusion proteins.

SUMMARY OF THE INVENTION

The purpose of the present invention is to provide a more effective anti-tumor fusion protein.

In a first aspect of the present invention, it provides a fusion protein, and the fusion protein has the structure as shown in Formula I or II from the N-terminus to the C-terminus:

Z1-L-Z2         (I)

Z2-L-Z1         (II)

wherein

Z1 is a CPP element;

L is no or a connecting element;

Z2 is a SH2 domain of SHP2 and/or SHP1 or an active fragment thereof;

"-" denotes a peptide bond or peptide linker connecting the above elements.

In another preferred embodiment, the Z1 and Z2 are connected in a head-to-head, head-to-tail, tail-to-head, or tail-to-tail manner.

In another preferred embodiment, the "head" refers to the N-terminus of a polypeptide or a fragment thereof, especially the N-terminus of a wild-type polypeptide or a fragment thereof.

In another preferred embodiment, the "tail" refers to the C-terminus of a polypeptide or a fragment thereof, especially the C-terminus of a wild-type polypeptide or a fragment thereof.

In another preferred embodiment, the Z1 and Z2 are D-type or L-type amino acids.

In another preferred embodiment, when the Z1 and Z2 are connected in a head-to-head manner, the Z1 and Z2 are L-type or D-type amino acids.

In another preferred embodiment, when the Z1 and Z2 are connected in a tail-to-tail manner, the Z1 and Z2 are L-type or D-type amino acids.

In another preferred embodiment, the CPP element is derived from a human or non-human mammal.

In another preferred embodiment, the CPP element includes wild type and mutant type.

In another preferred embodiment, the CPP element includes full-length, mature form of CPP, or an active fragment thereof, preferably 5-30 amino acids in length.

In another preferred embodiment, the CPP element is a TAT penetrating peptide.

In another preferred embodiment, the CPP element is selected from the group consisting of poly-L-arginine (R5-9), MPG, CADY, pVEC, Penetratin, Kaposi fibroblast growth factor peptide, VP22, and a combination thereof.

In another preferred embodiment, the sequence of the CPP element is shown in any one of SEQ ID NO.: 1, 15-21.

In another preferred embodiment, L consists of glycine and serine.

In another preferred embodiment, L has the following structure: -(Gly-Ser)n-; wherein, n is 1-5, preferably 1-3.

In another preferred embodiment, L has the following structure: -(Gly-Ser-Ser-Ser-Ser)n-; wherein, n is 1-5, preferably 1-3.

In another preferred embodiment, L contains 1-6 prolines, preferably 1-3 prolines.

In another preferred embodiment, the Z2 is derived from a human or non-human mammal.

In another preferred embodiment, the Z2 includes wild type and mutant type.

In another preferred embodiment, the Z2 comprises a full-length, mature form of the SH2 domain of SHP2 or SHP1, or an active fragment thereof.

In another preferred embodiment, Z2 is selected from the group consisting of N-terminal SH2 domain, C-terminal SH2 domain, and a combination thereof.

In another preferred embodiment, Z2 also includes an ITIM motif binding region of the C-terminal SH2 domain.

In another preferred embodiment, Z2 is the N-terminal SH2 domain of SHP2, with amino acids on positions 1-99 or 9-51 in SEQ ID NO.:2, preferably containing amino acids on positions 9, 28, 49 and 51 in SEQ ID No.: 2, and the length is 43-99 amino acids.

In another preferred embodiment, Z2 is the C-terminal SH2 domain of SHP2, having amino acids on positions 27-39 or 29-37 in SEQ ID NO.:3, preferably containing amino acids on positions 29, 31, 36 and 37 in SEQ ID NO.:3, and 9-108 or 13-108 amino acids in length.

In another preferred embodiment, Z2 is the N-terminal SH2 domain of SHP1, with amino acids on positions 9-51 in SEQ ID NO.:12, preferably containing amino acids on positions 9, 28, 49, 51 in SEQ ID NO.: 12 and 43-99 amino acids in length.

In another preferred embodiment, Z2 is the C-terminal SH2 domain of SHP1, having amino acids on positions 29-37 in SEQ ID NO.:13, preferably containing amino acids on positions 29, 31, 36, 37 in SEQ ID NO.: 13 and 9-107 amino acids in length.

In another preferred embodiment, Z2 has the structure as shown in Formula III from N-terminal to C-terminal:

A-L'-B                                     (III)

wherein
A is a N-terminal SH2 domain of SHP2 or SHP1 or an active fragment thereof;
L is no or a connecting element;
B is a C-terminal SH2 domain of SHP2 or SHP1 or an active fragment thereof;
"-" denotes a peptide bond or peptide linker connecting the above elements.

In another preferred embodiment, element A is the N-terminal SH2 domain of SHP2, having positions 1-99 or 9-51 in SEQ ID NO.: 2, preferably containing positions 9, 28, 49 and 51 in SEQ ID No.: 2 and 43-99 amino acids in length.

In another preferred embodiment, element B is the C-terminal SH2 domain of SHP2, having the sequence as shown in SEQ ID NO.:3, and containing positions 27-39 or 29-37 in SEQ ID NO.:3, preferably containing positions 29, 31, 36 and 37 in SEQ ID NO.:3, and 9-108 or 13-108 amino acids in length.

In another preferred embodiment, element A is the N-terminal SH2 domain of SHP1, with amino acids on positions 9-51 in SEQ ID NO.: 12, preferably containing amino acids on positions 9, 28, 49, 51 in SEQ ID NO.: 12, and 43-99 amino acids in length.

In another preferred embodiment, element B has the C-terminal SH2 domain of SHP1, having amino acids on positions 29-37 in SEQ ID NO.: 13, preferably containing amino acids on positions 29, 31, 36, 37 in SEQ ID NO.: 13, and the length is 9-107 amino acids.

In another preferred embodiment, the length of the L' is 1-20aa, preferably 3-15aa, more preferably 5-10aa.

In another preferred embodiment, the amino acid sequence of L' is selected from the group consisting of:
(1) a polypeptide whose amino acid sequence is shown in SEQ ID NO.: 10;
(2) a polypeptide derived from a polypeptide having the amino acid sequence shown in SEQ ID NO.: 10 having the function of the polypeptide described in (1) formed by substitution, deletion or addition of one or several, preferably 1-20, more preferably 1-15, more preferably 1-10, more preferably 1-8, more preferably 1-3, most preferably 1 amino acid residue (s) in the amino acid sequence as shown in SEQ ID NO.: 10.

In another preferred embodiment, Z2 has the sequence as shown in SEQ ID NO.: 11 or 14.

In another preferred example, the sequence of Z2 is shown in SEQ ID NO.: 11 or 14.

In another preferred embodiment, the length of the peptide linker is 0-10 amino acids, preferably 0-5 amino acids.

In another preferred embodiment, the fusion protein is selected from the group consisting of:
(A) a polypeptide having the amino acid sequence as shown in any of SEQ ID NOs: 4-8;
(B) a polypeptide having ≥80% homology (preferably, ≥90% homology; preferably ≥95% homology; most preferably, ≥97% homology, such as 98% or more, 99% or more) with the amino acid sequence as shown in any of SEQ ID NOs: 4-8, and the polypeptide has tumor suppressive activity;

(C) a derivative polypeptide which is formed by substitution, deletion or addition of 1-5 amino acid residues in the amino acid sequence as shown in any of SEQ ID NOs: 4-8 and retains the tumor suppressive activity.

In another preferred embodiment, the amino acid sequence of the fusion protein is shown in any of SEQ ID NO.: 4-8.

In a second aspect of the present invention, it provides an isolated polynucleotide encoding the fusion protein according to the first aspect of the present invention.

In another preferred embodiment, the polynucleotide additionally contains auxiliary elements selected from the group consisting of a signal peptide, a secretory peptide, a tag sequence (e.g., 6His), and a combination thereof, flanking the ORF of the mutant protein or fusion protein.

In another preferred embodiment, the polynucleotide is selected from the group consisting of DNA sequence, RNA sequence, and a combination thereof.

In a third aspect of the present invention, it provides a vector, which contains the polynucleotide as described in the second aspect of the present invention.

In another preferred embodiment, the vector comprises one or more promoters operably linked to the nucleic acid sequence, enhancer, transcription termination signal, polyadenylation sequence, origin of replication, selectable marker, nucleic acid restriction site, and/or homologous recombination site.

In another preferred embodiment, the vector includes a plasmid and viral vector.

In another preferred embodiment, the viral vector is selected from the group consisting of adeno-associated virus (AAV), adenovirus, lentivirus, retrovirus, herpes virus, SV40, poxvirus, and a combination thereof.

In another preferred embodiment, the vector includes an expression vector, a shuttle vector, and an integration vector.

In a fourth aspect of the present invention, it provides a host cell, the host cell contains the vector of the third aspect of the present invention, or the polynucleotide of the second aspect of the present invention is integrated into its genome.

In another preferred embodiment, the host cell is an eukaryotic cell, such as yeast cell, plant cell or mammalian cell (including a human and non-human mammal).

In another preferred embodiment, the host cell is a prokaryotic cell, such as Escherichia coli.

In another preferred embodiment, the yeast cell is selected from one or more sources of yeast from the group consisting of: Pichia pastoris, Kluyveromyces and a combination thereof; preferably, the yeast cell includes: Kluyveromyces, more preferably Kluyveromyces marxianus, and/or Kluyveromyces lactis.

In another preferred embodiment, the host cell is selected from the group consisting of Escherichia coli, wheat germ cell, insect cell, SF9, Hela, HEK293, CHO, yeast cell, and a combination thereof.

In a fifth aspect of the present invention, it provides a method for producing the fusion protein of the first aspect of the present invention, the method comprising the steps of:
Under conditions suitable for expression, culturing the host cell according to the fourth aspect of the present invention, thereby expressing the fusion protein; and/or isolating the fusion protein.

In a sixth aspect of the present invention, it provides a pharmaceutical composition comprising the fusion protein of the first aspect of the present invention and a pharmaceutically acceptable carrier thereof.

In another preferred embodiment, the pharmaceutical composition further includes other drugs for inhibiting tumor activity.

In another preferred embodiment, other drugs for inhibiting tumor activity are selected from the group consisting of: PD-1 antibody, PD-L1 antibody, HER2 monoclonal antibody, BTLA antibody, CTLA-4 antibody, CD47 antibody, NKG2A antibody, NKTR-214, GDF-15 antibody, LILRB4 antibody, LAIR1 antibody, Tim-3 antibody, Lag-3 antibody, Tight antibody, CD160 antibody, KLRG-1 antibody, GP49B antibody, CD31 antibody, CD38 antibody, Lair-1 antibody, CD200/CD200R antibody, Catumaxomab, Blinatumomab, EGFR monoclonal antibody, CD20 monoclonal antibody, VEGF/VEGFR monoclonal antibody, Licartin, Zevalin, Bexxar, Mylotarg, Kadcyla, Aflibercept, Conbercept, Apalutamide (ARN-509), Rova-T, TNFα, IFNγ, IL-2, Tβ4, EGFR-targeted small molecule inhibitors, paclitaxel (PTX), docetaxel (TXT), cisplatin (DDP), carboplatin (CBP), oxaliplatin, nedaplatin, cyclophosphamide (CTX), ifosfamide (IFO), doxorubicin (ADM), pirarubicin (THP), Epirubicin (EPI), Fluorouracil (5-Fu), Gemcitabine (GEM), Vinorelbine (NVB), Pemetrexed (PEM), Irinotecan (CPT-11), etoposide (VP-16), capecitabine (Xeloda), leuprolide acetate, goserelin acetate, and a combination thereof.

In another preferred embodiment, the PD-1 antibody is selected from the group consisting of: nivolumab, pembrolizumab, cemiplimab, Toripalimab, Sintilimab, camrelizumab, Tislelizumab, and a combination thereof.

In another preferred embodiment, the PD-L1 antibody is selected from the group consisting of atezolizumab, durvalumab, avelumab, and a combination thereof.

In another preferred embodiment, the HER2 monoclonal antibody is selected from the group consisting of trastuzumab, pertuzumab, T-DM1, and a combination thereof.

In another preferred embodiment, the CTLA-4 antibody includes Ipilimumab.

In another preferred embodiment, the EGFR monoclonal antibody includes Necitumumab, Panitumumab, Nimotuzumab, and Cetuximab.

In another preferred embodiment, the CD20 monoclonal antibody is selected from the group consisting of rituximab, Ibritumomab, Tositumomab, ofatumumab, Ocrelizumab, and obinutuzumab, and a combination thereof.

In another preferred embodiment, the VEGF/VEGFR monoclonal antibody is selected from the group consisting of bevacizumab, Ramucirumab, Lucentis, and a combination thereof.

In another preferred embodiment, the EGFR-targeted small molecule inhibitor is selected from the group consisting of erlotinib, gefitinib, icotinib, afatinib (including afatinib dimaleate, Dacomitinib, osimertinib, Nazartinib, neratinib (including neratinib maleate), sorafenib, Apatinib (such as Apatinib Mesylate Tablets), imatinib, sunitinib, dasatinib, lapatinib, Pazopanib, crizotinib, vandetanib, Regorafenib, axitinib, ponatinib, neratinib, Zanubrutinib, anlotinib, ceritinib, Fruquintinib, Pyrotinib, lenvatinib, and a combination thereof.

In a seventh aspect of the present invention, it provides a use of the fusion protein as described in the first aspect of the present invention, the polynucleotide as described in the second aspect of the present invention, the vector as described in the third aspect of the present invention, and the host cell as described in the fourth aspect of the present invention for preparing a composition or preparation, the composition or preparation is used for the treatment or prevention of tumor.

In another preferred embodiment, the composition or preparation is also used for one or more purposes selected from the group consisting of:

(a) enhancing the killing effect of T cells on tumor cells;
(b) inhibiting tumor growth;
(c) inhibiting the apoptosis of T cells;
(d) increasing the level of IL-2 secreted by T cells;
(e) enhancing the killing effect of NK cells on tumor cells;
(f) increasing the expression level of CD107a in NK cells;
(g) increasing the secretion of perforin and granzyme from NK cells;
(h) increasing the secretion of IFN-γ and TNF-α in NK cells;
(i) enhancing the phagocytic function of macrophages;
(j) enhancing the phagocytosis and killing of tumor cells by macrophages;
(k) increasing the secretion of NO, TNF-α and IL-1β in macrophages.

In another preferred embodiment, the composition is a pharmaceutical composition.

In another preferred embodiment, the tumor is selected from the group consisting of breast cancer, colon cancer, lung cancer, colorectal cancer, gastric cancer, esophagus cancer, pancreatic cancer, ovarian cancer, prostate cancer, kidney cancer, liver cancer, brain cancer, melanoma, multiple myeloma, leukemia, lymphoma, head and neck tumor, thyroid cancer, and a combination thereof.

In another preferred embodiment, the tumor cells are from one or more tumors selected from the group consisting of breast cancer, colon cancer, lung cancer, colorectal cancer, gastric cancer, esophagus cancer, pancreatic cancer, ovarian cancer, prostate cancer, kidney cancer, liver cancer, brain cancer, melanoma, multiple myeloma, leukemia, lymphoma, head and neck tumor, thyroid cancer, and a combination thereof.

In an eighth aspect of the present invention, it provides an in vitro non-therapeutic method for inhibiting tumor growth, comprising the steps of:

In the presence of the fusion protein according to the first aspect of the present invention, culturing a tumor cell, thereby inhibiting the tumor growth.

In another preferred embodiment, the tumor cell is from one or more tumors selected from the group consisting of breast cancer, colon cancer, lung cancer, colorectal cancer, gastric cancer, esophagus cancer, pancreatic cancer, ovarian cancer, prostate cancer, kidney cancer, liver cancer, brain cancer, melanoma, multiple myeloma, leukemia, lymphoma, head and neck tumor, thyroid cancer, and a combination thereof.

In another preferred embodiment, the tumor cell is a cell cultured in vitro.

In a ninth aspect of the present invention, it provides a method for treating tumors, comprising the step of: administering the fusion protein as described in the first aspect of the present invention to a subject in need.

In another preferred embodiment, the fusion protein is administered in the form of monomers and/or dimers.

In another preferred embodiment, the subject is a human.

It should be understood that, within the scope of the present invention, each technical feature of the present invention described above and in the following (as examples) may be combined with each other to form a new or preferred technical solution, which is not listed here due to space limitations.

DESCRIPTION OF FIGURE

FIG. 1 shows the double enzyme digestion identification results of pET-22b(+)TAT-SHP2-N-SH2.

FIG. 2 shows the sequencing results of the recombinant plasmid pET-22b(+)TAT-SHP2-N-SH2.

FIG. 3 shows the expression of the target protein detected by SDS-PAGE;

1 Marker; 2 not induced; 3 IPTG induced 1; 4 IPTG induced 2; the red arrow points to the target protein.

FIG. 4 shows the expression of the target protein detected by SDS-PAGE;

Note: 1 uninduced, 2 induced, 3 lysed supernatant, 4 lysed pellet.

FIG. 5 shows the separation of target protein and impure protein by cation exchange chromatography;

Note: SP1-SP4 are elution peaks, of which SP4 is the peak where the target protein is located.

FIG. 6 shows the purification effect of TAT-SHP2-N-SH2 detected by SDS-PAGE;

Note: 1 pass, 2 SP1, 3 SP2, 4 SP3, 5 SP4 (target protein peak).

FIG. 7 shows the identification of SHP2-N-SH2 target protein by Western-blot;

1 IPTG-uninduced recombinant bacteria; 2 1 mM IPTG-induced recombinant bacteria.

FIG. 8 shows chromatographic analysis results of HPLC purification of fusion protein.

FIG. 9 shows the results of chromatographic analysis of polypeptide HPLC purification;

A, L1 polypeptide; B, L2 polypeptide; C, D1 polypeptide; D, D2 polypeptide.

FIG. 10 shows the molecular weight of peptides detected by mass spectrometry; A, L1 peptide; B, L2 peptide; C, D1 peptide; D, D2 peptide.

FIG. 11 shows the localization of fusion proteins and polypeptides in T cells detected by confocal laser;

a. The ability to enter cells without TAT transmembrane sequence control peptide (20 μg/mL) is observed under confocal microscope; b. SHP2-C-SH2 with TAT sequence; c. SHP2-N-SH2 with TAT sequence; the action times are 0, 0.5, 4, 24, 72, 96, 120 and 144 h (25 μm (×60).

FIG. 12 shows the effect of recombinant TAT-N-SH2 fusion protein and L1 polypeptide on T lymphocyte proliferation;

a-c CFSE method is used to detect the effect of different treatment groups on T lymphocyte proliferation. d According to the results of flow cytometry, the proportion of T cell proliferation is counted. Compared with the control group, p>0.05 has no statistical significance.

FIG. 13 shows the effect of recombinant TAT-N-SH2 fusion protein and L1 polypeptide on T lymphocyte apoptosis;

a-d Annexin V-FITC is used to detect the effect of peptides on apoptosis of T lymphocytes. The resuspended cells are added to different groups to treat untreated groups SHP2-NC, SHP2-N-SH2 (80 μg/mL), TAT-SHP2-C-SH2 polypeptide (80 μg/mL), and then continues to culture on EASY-T stimulated plates for 3 d (50 ng of PD-L1 antibody is added 3 hours before adding the cell mixture to coat a 24-well plate at 37° C.), and the cells are collected, detection by flow cytometry after FITC and PI staining; e According to the results of flow cytometry, the proportion of apoptotic cells is counted, compared with the control group, *p<0.05 or **p<0.01.

FIG. 14 shows the effect of fusion proteins and polypeptides on the phosphorylation level of T cell-mediated downstream signaling molecules;

a. TAT-SHP2-N-SH2 fusion protein treatment group; c. TAT-SHP2 C-SH2 polypeptide treatment group; b, d. According to Western-blot results, with β-actin as an internal reference, grayscale analysis of the phosphorylation expression of JNK, AKT and ERK proteins mediated by T lymphocytes is performed. Unpaired t-test, compared with negative control, **p<0.01, NS has no statistical difference.

FIG. 15 shows the detection of cytokine IL-2 secreted by T cells;

Unpaired t-test, compared to control, *p<0.05 and ****p<0.0001.

FIG. 16 shows the results of detection of direct tumor-killing effect.

FIG. 17 shows killing effect of TAT-SHP2-N-SH2 fusion protein on different tumor cell lines by stimulating T cells. Compared with the untreated group, *p<0.05 or p<0.01 or *p<0.001, p>0.05 is not statistically significant.

FIG. 18 shows the killing effect of TAT-SHP2-C-SH2 polypeptide stimulating T cells on different tumor cell lines. Compared with the untreated group, *p<0.05 or p<0.01 or *p<0.001, p>0.05 is not statistically significant.

FIG. 19 shows the killing effect of L1, L2, D1, and D2 polypeptides on lung cancer cell H460 by stimulating T cells;

Compared with the control group, *P<0.05, P<0.01, *P<0.001, ****P<0.0001;

Compared with D2 group, #P<0.05, ##P<0.01, ###P<0.001.

FIG. 20 shows the tumor suppressive effect of TAT-SHP2-N-SH2 fusion protein on colon cancer tumor-bearing mice;

a. Tumor weight of mice in different dose groups after dissection 30 days; b. Tumor size; Unpaired t-test, compared with control group, *p<0.05, p<0.01, *p<0.001 and ****p<0.0001.

FIG. 21 shows the antitumor effect of TAT-SHP2-C-SH2 polypeptide on colon cancer tumor-bearing mice;

a. Tumor weight of mice in different dose groups after 30 d dissection; b. Tumor size; Unpaired t-test, compared with control group, p<0.01, *p<0.001 and ****p<0.0001.

FIG. 22 shows the antitumor effect of TAT-SHP2-N-SH2 fusion protein and TAT-SHP2-C-SH2 polypeptide on breast cancer tumor-bearing mice;

a. Tumor weight of mice in different administration groups after 21 d dissection; b. Tumor size; Unpaired t-test, compared with control group, *p<0.05, p<0.01, *p<0.001.

FIG. 23 shows the antitumor effect of recombinant TAT-N-SH2 fusion protein and L1 polypeptide on colon cancer nude mice;

a. Tumor weight of mice after 30 d dissection; b. Tumor size; c. Tumor growth curve; Unpaired t-test, compared with control group, NS: no statistical difference.

FIG. 24 shows the tumor suppressive effect of recombinant TAT-N-SH2 fusion protein and L1 polypeptide on breast cancer in nude mice;

a. Tumor weight of mice after 21 d dissection; b. Tumor size; c. Tumor growth curve; NS: no statistical difference.

FIG. 25 shows the antitumor effect of recombinant TAT-N-SH2 fusion protein and L1 polypeptide on PD-L1 knock-out breast cancer tumor-bearing mice;

a. Tumor weight of mice after 23 d dissection; b. Tumor size; c. Tumor growth curve; Unpaired t-test, compared with control group, *P<0.05, P<0.01, *P<0.001.

FIG. 26 shows the detection of anti-tumor effect of L1, L2, D1, D2 polypeptides on mouse lung cancer;

a. Tumor weight of mice after 21 d dissection; b. Tumor size; c. Tumor growth curve; Unpaired t-test, compared with control group, *P<0.05, P<0.01, *P<0.001.

DETAILED DESCRIPTION

After in-depth research, the inventors have unexpectedly found a fusion protein containing CPP elements, optional linking elements and the SH2 domain of SHP2 or SHP1 or an active fragment thereof. The fusion protein obtained by the present invention has extremely excellent killing activity against tumors, and the fusion protein of the present invention can also significantly enhance the killing effect of T cells on tumor cells. The present invention has been completed on this basis.

CPP Element

The cell membrane is the main barrier between cells and the extracellular environment. Because of this natural barrier, it is difficult for many biological macromolecules to penetrate the cell membrane and enter the cell, which is a major obstacle to targeted drug delivery at this stage. Cell penetrating peptides (CPPs) are a class of polypeptides composed of 5-30 amino acid residues with cell membrane penetrating ability, which can carry biological macromolecules such as proteins and nucleic acids into cells. CPP-mediated entry of biological macromolecules into cells is the most successful delivery system that can directly transport biological macromolecules in vivo and in vitro due to safer and more efficient than traditional methods. The earliest CPP study found that an arginine-rich polypeptide (TAT) in the transactivation transcription protein of human immunodeficiency virus (HIV-1) can effectively cross the cell membrane and activate the transcription of the corresponding viral promoter. TAT can efficiently deliver drugs into cells. The transmembrane function of TAT was precisely located in the 11-amino acid core segment (aa47-aa57), which was named as the TAT-protein transduction domain (TAT-PTD), and was successfully applied to different intracellular transport of foreign proteins.

CPPs can be divided into three categories according to their chemical properties: (1) Cationic, rich in arginine and lysine residues, with a strong positive charge at physiological pH, mainly including TAT, R9, hLF, etc. (2) The positive charge of amphiphilic peptides is provided by lysine residues, such CPPs contain hydrophobic and hydrophilic domains, and their amphipathic characteristics are jointly determined by its primary and secondary structures. It mainly includes MPG, CADY, pVEC, SAP and so on. (3) Hydrophobic CPPs have lower net charges and are mainly composed of non-polar amino acids. Such as Kaposi fibroblast growth factor (K-FGF) peptide.

In a preferred embodiment, the CPP element of the present invention is a TAT penetrating peptide.

In a preferred embodiment, the CPP element of the present invention is selected from the group consisting of poly-L-arginine (R5-9), MPG (consisting of the fusion protein domain of the gp41 protein of human autoimmune deficiency virus type 1 and the nuclear localization sequence region of the simian vacuolar virus large T antigen, the amino acid sequence:

GLAFLGFLGAAGSTMGAWSQPKKKRKV (SEQ ID NO.: 15)), CADY (a secondary amphiphilic peptide consisting of 20 amino acids containing tryptophan residues and arginine residues, the amino acid sequence: GLWRALWRLLRSLWRLLWKA (SEQ ID NO. 16)-CyA), pVEC (derived from murine vascular endothelial cell cadherin, the amino acid sequence: LLIILRRRIRKQAHAHSK (SEQ ID NO.: 17)), Penetratin (sequences 43-58 with more positive charges in the third α-helix of *Drosophila* antennal homeotic transcription factor protein, the amino acid sequence: RQIKIWFQNRRMKWKK (SEQ ID NO.: 18)), Kaposi fibroblast growth factor peptide (K-FGF, amino acid sequence: AAVLLPVLLAAP (SEQ ID NO.: 19)), VP22 (herpes simplex virus type 1 intermediate layer protein, amino acid sequence: DAATATRGRSAASRPTER-PRAPARSASRPRRVD (SEQ ID NO.:20)), and a combination thereof.

Immunoreceptor Tyrosine-Based Inhibitory Motif (ITIM)

At present, most of the immune checkpoint inhibitory receptors (PD-1, BTLA, KIR, CD31 and SIRPα, etc.) are known. Although their extracellular regions are different, they all contain one or more immunoreceptor tyrosine based inhibitor motifs (ITIMs) in their intracellular segments, when the tyrosine in ITIM is phosphorylated, it can recruit the signaling molecule protein tyrosine phosphatase 1 or 2 (SH2 domain-containing inositol phosphatase-1, SHP1; SH2 domain-containing inositol phosphatase-2, SHP2), triggers the production of inhibitory signals that result in incapacitation and/or apoptosis of effector T cells. Therefore, ITIM is a common domain that exerts inhibitory effects on many immune checkpoints, and it is also a key target for the design of generic drugs against immune checkpoints. SHP1 and SHP2 are highly homologous and are frequently recruited to the same binding sites, and the distinct roles of SHP1 and SHP2 phosphatases are currently unclear.

SHP1

Protein tyrosine phosphatase-1 (SH2 domain-containing protein tyrosine phosphates, SHP1) is mainly expressed in various human hematopoietic cells and is an important negative regulator that controls the level of phosphorylated tyrosine in the signaling pathway between lymphocytes. SHP1 contains two SH2 domains, N-SH2 (3-101) and C-SH2 (109-215), a catalytic (PTP) domain (272-514), a tail rich in proline groups and tyrosine phosphorylation sites.

SHP2

SHP2 is a protein tyrosine phosphatase encoded by the human non-receptor protein tyrosine phosphatase 11 (Protein Tyrosine Phosphatase, Non Receptor Type 11, PTPN11) gene, containing two SH2 domains, respectively N-SH2 (5-103) and C-SH2 (111-218), a catalytic (PTP) domain (276-523), a tail rich in proline groups and tyrosine phosphorylation sites. The PTPN11 gene comprises 16 exons and produces a ubiquitously expressed 7 kb transcript containing a 1.779 bp open reading frame encoding a 593 amino acid protein. In addition, human and mouse SHP2 gene sequence homology is 100%.

In the inactive state (inactive) the N-SH2 domain of SHP2/SHP1 makes extensive contacts with the catalytic domain PTP through charge-charge interactions, and part of the SH2 domain (NXGDY/F motif) is inserted into the catalytic cracks, preventing the substrate from entering the active site and loses catalytic activity. When a ligand containing phosphorylated tyrosine residues binds to the N-SH2 domain, the conformational change switch in the SH2 domain changes from an inactive state to an active state. This conformational change in the N-SH2 domain of SHP2/SHP1 disrupts the interaction between the SH2 domain and the phosphatase domain, abolishing self-inhibition and allowing substrate entry.

In the present invention, by blocking the combination of the N-SH2 and C-SH2 domains of SHP2/SHP1 in immune cells and ITIM as the starting point, Fusion proteins and mimetic polypeptides of N-SH2 and C-SH2 domains of SHP2/SHP1 that can bind to ITIM were designed and prepared by using genetic engineering and polypeptide solid-phase synthesis techniques. In order to enable the fusion protein and polypeptide to enter cells, the transmembrane peptide TAT is fused to the N-terminus of the fusion protein and the C-terminus of the polypeptide. The transactivator protein (TAT) of HIV1 can efficiently and rapidly introduce polypeptides and proteins into cells without affecting the normal structure and function of cells. After the fusion proteins and polypeptides enter the cells, they can compete with the normally expressed SHP2/SHP1 in T lymphocytes to bind to the ITIM of the intracellular segment of the inhibitory receptor, so that the SHP2/SHP1 in the immune cells are always in an inactive state, thereby inactivating the inhibitory effect of immunosuppressive receptors, which is the development idea of the general immune checkpoint inhibitor designed in the present invention with ITIM as the target.

Fusion Protein

As used herein, "fusion protein of the present invention", or "polypeptide" refers to the fusion protein of the first aspect of the present invention.

In another preferred embodiment, the structure of the fusion protein is shown as Z1-L-Z2 (I) or Z2-L-Z1 (II), wherein B is CCP protein; L is no or connecting element; and Z2 is the SH2 domain of SHP2 or SHP1 or an active fragment thereof.

In another preferred embodiment, the fusion protein has the amino acid sequence as shown in any of SEQ ID NO.: 4-8.

As used herein, the term "fusion protein" also includes variant forms of fusion proteins (such as the sequences set forth in any of SEQ ID NO.: 4-8) having the above-mentioned activities. These variants include (but are not limited to): deletions, insertions and/or substitutions of 1-3 (usually 1-2, more preferably 1) amino acids, and additions or deletions of one or several (usually within 3, preferably within 2, more preferably within 1) amino acids at the C-terminus and/or N-terminus. For example, in the art, substitutions with amino acids of close or similar properties generally do not alter the function of the protein. For another example, addition or deletion of one or several amino acids at the C-terminus and/or N-terminus usually does not alter the structure and function of the protein. Furthermore, the term also includes monomeric and multimeric forms of the polypeptides of the invention. The term also includes linear as well as nonlinear polypeptides (e.g., cyclic peptides).

The present invention also includes active fragments, derivatives and analogs of the above fusion proteins. As used herein, the terms "fragment", "derivative" and "analog" refer to polypeptides that substantially retain the function or activity of the fusion proteins of the present invention. The polypeptide fragments, derivatives or analogs of the present invention may be (i) a polypeptide in which one or several conservative or non-conservative amino acid residues (preferably conservative amino acid residues) have been substituted, or (ii) a polypeptide having a substituent group in one or more amino acid residues, or (iii) a polypeptide formed by fusion of an antigenic peptide with another compound (such as a compound that prolongs the half-life of a polypeptide, such as polyethylene glycol), or (iv) a polypeptide formed by fusing an additional amino acid sequence with this polypeptide sequence (a fusion protein formed by fusing with a leader sequence, a secretory sequence, or a tag sequence such as 6xHis). These fragments, derivatives and analogs are well known to those skilled in the art in light of the teachings herein.

A class of preferred active derivatives refers to that compared with the amino acid sequence of Formula I or Formula II, at most 3, preferably at most 2, more preferably at most 1 amino acid is replaced by amino acids with close or similar properties to form a polypeptide. These conservatively variant polypeptides are best produced by amino acid substitutions according to Table A.

TABLE A

| initial residue | representative substitution | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention also provides analogs of the fusion proteins of the present invention. The differences between these analogs and the polypeptides shown in any of SEQ ID NO.:4-8 may be differences in amino acid sequence, differences in modified forms that do not affect the sequence, or both. Analogs also include analogs with residues other than natural L-amino acids (e.g., D-amino acids), as well as analogs with non-naturally occurring or synthetic amino acids (e.g., beta, gamma-amino acids). It should be understood that the polypeptides of the present invention are not limited to the representative polypeptides as exemplified above.

Modified (generally without altering the primary structure) forms include chemically derivatized forms such as acetylation or carboxylation of the polypeptide in vivo or in vitro. Modifications also include glycosylation, such as those resulting from glycosylation modifications in the synthesis and processing of the polypeptide or in further processing steps. Such modifications can be accomplished by exposing the polypeptide to enzymes that perform glycosylation, such as mammalian glycosylases or deglycosylases. Modified forms also include sequences with phosphorylated amino acid residues (eg, phosphotyrosine, phosphoserine, phosphothreonine). Also included are polypeptides that have been modified to increase their resistance to proteolysis or to optimize their solubility properties.

Expression Vectors and Host Cells

The present invention also relates to vectors comprising the polynucleotides of the present invention, as well as host cells produced by genetic engineering with the vectors of the present invention or the coding sequences of fusion proteins of the present invention, and methods for producing the polypeptides of the present invention by recombinant techniques.

The polynucleotide sequences of the present invention can be used to express or produce recombinant fusion proteins by conventional recombinant DNA techniques. Generally there are the following steps:

(1). Use the polynucleotide (or variant) encoding the fusion protein of the present invention of the present invention, or transform or transduce a suitable host cell with a recombinant expression vector containing the polynucleotide;

(2). Host cells cultured in a suitable medium;

(3). Separation and purification of proteins from culture medium or cells.

In the present invention, the polynucleotide sequence encoding the fusion protein can be inserted into a recombinant expression vector. The term "recombinant expression vector" refers to bacterial plasmids, bacteriophages, yeast plasmids, plant cell viruses, mammalian cell viruses such as adenoviruses, retroviruses, or other vectors well known in the art. Any plasmids and vectors can be used as long as they are replicable and stable in the host. An important feature of expression vectors is that they typically contain an origin of replication, a promoter, marker genes and translational control elements.

Methods well known to those skilled in the art can be used to construct expression vectors containing the DNA sequences encoding the fusion proteins of the invention and appropriate transcriptional/translational control signals. These methods include in vitro recombinant DNA technology, DNA synthesis technology, in vivo recombinant technology, and the like. The DNA sequence can be operably linked to an appropriate promoter in an expression vector to direct mRNA synthesis. Representative examples of these promoters are: the lac or trp promoter of *E. coli*; the bacteriophage lambda PL promoter; eukaryotic promoters including the CMV immediate early promoter, the HSV thymidine kinase promoter, the early and late SV40 promoters, LTRs of retroviruses and some other known promoters that control the expression of genes in prokaryotic or eukaryotic cells or their viruses. Expression vectors also include a ribosome binding site for translation initiation and a transcription terminator.

In addition, the expression vector preferably contains one or more selectable marker genes to provide phenotypic traits for selection of transformed host cells, such as dihydrofolate reductase for eukaryotic cell culture, neomycin resistance, and green fluorescent protein (GFP), or Tetracycline or ampicillin resistance for *E. coli*.

Vectors comprising the appropriate DNA sequences described above, together with appropriate promoter or control sequences, can be used to transform appropriate host cells so that they can express the protein.

Host cells can be prokaryotic cells (eg, *E. coli*), or lower eukaryotic cells, or higher eukaryotic cells, such as yeast cells, plant cells, or mammalian cells (including humans and non-human mammals). Representative examples are: *Escherichia coli*, wheat germ cells, insect cells, SF9, Hela, HEK293, CHO, yeast cells, etc. In a preferred embodiment of the present invention, select yeast cells (such as *Pichia pastoris, Kluyveromyces*, or a combination thereof; preferably, the yeast cells include: *Kluyveromyces*, more preferably *Kluyveromyces marxianus*, and/or *Kluyveromyces lactis*) as the host cell.

When the polynucleotides of the present invention are expressed in higher eukaryotic cells, transcription will be enhanced if an enhancer sequence is inserted into the vector. Enhancers are cis-acting elements of DNA, usually about 10 to 300 base pairs in length, that act on a promoter to enhance transcription of a gene. Illustrative examples include the 100 to 270 base pair SV40 enhancer on the late side of the replication origin, the polyoma enhancer on the late side of the replication origin, and adenovirus enhancers, among others.

It will be clear to those of ordinary skill in the art how to select appropriate vectors, promoters, enhancers and host cells.

Transformation of host cells with recombinant DNA can be performed using conventional techniques well known to those skilled in the art. When the host is a prokaryotic organism such as *E. coli*, competent cells capable of uptake of DNA can be harvested after exponential growth phase and treated with the CaCl$_2$) method using procedures well known in the art. Another way is to use MgCl$_2$. If desired, transformation can also be performed by electroporation. When the host is a eukaryotic organism, the following DNA transfection methods can be used: calcium phosphate co-precipitation method, conventional mechanical methods such as microinjection, electroporation, liposome packaging and the like.

The obtained transformants can be cultured by conventional methods to express the polypeptides encoded by the genes of the present invention. The medium used in the culture can be selected from various conventional media depending on the host cells used. Cultivation is carried out under conditions suitable for growth of the host cells. After the host cells have grown to an appropriate cell density, the promoter of choice is induced by a suitable method (eg, temperature switching or chemical induction), and the cells are cultured for an additional period of time.

The recombinant polypeptide in the above method can be expressed intracellularly, or on the cell membrane, or secreted outside the cell. If desired, recombinant proteins can be isolated and purified by various isolation methods utilizing their physical, chemical and other properties. These methods are well known to those skilled in the art. Examples of such methods include, but are not limited to: conventional renaturation treatment, treatment with protein precipitants (salting-out method), centrifugation, osmotic disruption, ultratreatment, ultracentrifugation, molecular sieve chromatography (gel filtration), adsorption chromatography, ion exchange chromatography, high performance liquid chromatography (HPLC) and various other liquid chromatography techniques and combinations of these methods.

Peptide Linker

The present invention provides a fusion protein, which may optionally contain a peptide linker. Peptide linker size and complexity may affect protein activity. In general, the peptide linker should be of sufficient length and flexibility to ensure that the two proteins connected have enough degrees of freedom in space to exert their functions. At the same time, the influence of the formation of α helix or β sheet in the peptide linker on the stability of the fusion protein is avoided.

The length of the linker peptide is generally 0-10 amino acids, preferably 0-5 amino acids.

Pharmaceutical Composition

The present invention also provides a pharmaceutical composition. In a preferred example, the composition is a pharmaceutical composition, which contains the above-mentioned fusion protein, and a pharmaceutically acceptable carrier, diluent, stabilizer and/or thickener, and can be prepared as a lyophilized powder, Tablet, Capsule, Syrup, Solution or Suspension.

"Pharmaceutically acceptable carrier or excipient" means: one or more compatible solid or liquid filler or gel substances, which are suitable for human use and which must be of sufficient purity and sufficient low toxicity. "Compatibility" as used herein means that the components of the composition can be blended with the active ingredients of the present invention and with each other without significantly reducing the efficacy of the active ingredients.

Compositions may be liquid or solid, such as powders, gels or pastes. Preferably, the composition is a liquid, preferably an injectable liquid. Suitable excipients will be known to those skilled in the art.

Examples of pharmaceutically acceptable carrier moieties include cellulose and its derivatives (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agents (such as Sodium lauryl Sulfates), colorants, flavouring agents, stabilizers, antioxidants, preservatives, pyrogen-free water, etc.

The compositions may comprise physiologically acceptable sterile aqueous or anhydrous solutions, dispersions, suspensions or emulsions, and sterile powders for reconstitution into sterile injectable solutions or dispersions. Suitable aqueous and non-aqueous carriers, diluents, solvents or excipients include water, ethanol, polyols and suitable mixtures thereof.

Generally, these materials can be formulated in a nontoxic, inert and pharmaceutically acceptable aqueous carrier medium, usually at a pH of about 5-8, preferably at a pH of about 6-8, although the pH may vary depending on the nature of the substance being formulated and the condition being treated. The formulated pharmaceutical compositions can be administered by conventional routes including, but not limited to, intraperitoneal, intravenous, or topical administration. The pharmaceutical composition is used for (a) treating or preventing tumors; (b) enhancing the killing effect of T cells on tumor cells; (c) inhibiting the growth of tumors; (d) inhibiting the apoptosis of T cells; (e) increasing the level of IL-2 secreted by T cells. (a) Enhancing the killing effect of NK cells on tumor cells; (b) Increasing the expression level of CD107a in NK cells; (c) Increasing the secretion of perforin and granzyme in NK cells; (d) Increasing the secretion of IFN-γ and TNF-α in NK cells; (a) enhancing the phagocytic function of M cells; (b) enhancing the phagocytosis and killing of tumor cells by M cells; (c) increasing the secretion of NO, TNF-α and IL-1β from M cells.

The main advantages of the present invention include:
(a) The present invention finds a fusion protein for the first time, the fusion protein contains CCP protein, an optional connection element and the SH2 domain of SHP2 or SHP1 or its active fragment, and the fusion protein obtained by the present invention has extremely excellent tumor-killing activity.
(b) The fusion protein of the present invention can also significantly enhance the killing effect of T cells on tumor cells; and/or inhibit the growth of tumors; and/or inhibit the apoptosis of T cells; and/or increase the level of IL-2 secreted by T cells.
(c) The fusion protein of the present invention can also enhance the killing effect of NK cells on tumor cells; increase the expression level of CD107a in NK cells; increase the secretion of perforin and granzyme in NK cells; and increase the secretion of IFN-γ and TNF-α in NK cells.

(d) The fusion protein of the present invention can also enhance the phagocytic function of macrophages; enhance the phagocytosis and killing effect of macrophages on tumor cells; and increase the secretion of NO, TNF-α and IL-1β of macrophages.
(e) For the first time, the present invention takes blocking the binding of the N-SH2 and C-SH2 domains of SHP2 or SHP1 to ITIM in immune cells as the starting point, and uses genetic engineering and polypeptide solid-phase synthesis technology to design and prepare fusion proteins and mimic peptides of SHP2 or SHP1 N-SH2 and C-SH2 domains that can bind to ITIM, respectively. In order to enable the fusion protein and polypeptide to enter cells, the transmembrane peptide TAT is fused to the N-terminus of the fusion protein and the C-terminus of the polypeptide. The transactivator protein (TAT) of HIV1 can efficiently and rapidly introduce polypeptides and proteins into cells without affecting the normal structure and function of cells. After fusion proteins and polypeptides enter cells, they can compete with SHP2 or SHP1 normally expressed in T lymphocytes/NK cells/macrophages to bind to ITIM in the intracellular segment of inhibitory receptors, so that SHP2 or SHP1 in immune cells is always in inactive state, thereby inactivating the inhibitory effect of immunosuppressive receptors.
(d) The fusion protein of the present invention has a broad-spectrum anti-tumor effect.

The present invention will be further described below in conjunction with specific embodiments. It should be understood that these examples are only used to illustrate the present invention and not to limit the scope of the present invention. The experimental method of unreceipted specific conditions in the following examples, usually according to normal conditions, people such as Sambrook, molecular cloning: conditions described in laboratory manual (New York: Cold Spring Harbor Laboratory Press, 1989), or according to manufacture conditions recommended by the manufacturer. Percentages and parts are weight percentages and parts unless otherwise specified.

Unless otherwise specified, the reagents and materials in the examples of the present invention are all commercially available products.

Example 1 Recombinant TAT-N-SH2 Fusion Protein and its Preparation Method

The recombinant TAT-N-SH2 fusion protein of the present invention connects the TAT penetrating peptide and N-SH2 through glycine and serine (TAT-N-SH2), and the connection method is: TAT-Gly-Ser-N-SH2; Its amino acid sequence is shown in SEQ ID NO.:4.

The nucleotide sequence of the recombinant TAT-N-SH2 fusion protein was the nucleotide sequence of connecting the TAT penetrating peptide and the N-terminal SH2 domain of SHP2 with a BamHI Restriction Enzyme cutting site, and an NdeI Restriction Enzyme cutting site was added at the 5' end, a termination codon TGA and a SalI Restriction Enzyme cutting site were added to the 3' end, and the connection method was: NdeI Restriction Enzyme cutting site -TAT gene-BamHI Restriction Enzyme cutting site –N-SH2 gene-TGA-SalI Restriction Enzyme cutting site, its nucleotide sequence is shown in SEQ ID NO.:9.

Recombinant TAT-N-SH2 fusion protein nucleotides were constructed in expression vector or recombinant plasmid pET-22b(+)-TAT-N-SH2, by NdeI Restriction Enzyme cutting site and SalI NdeI Restriction Enzyme cutting site, the plasmid pET-22b(+) was ligated with the recombinant TAT-N-SH2 fusion protein nucleotides of claim 3 by double digestion to obtain the pET-22b(+)-TAT-N-SH2.

The preparation method of recombinant TAT-N-SH2 fusion protein, according to the following steps:

1. Construction of Recombinant TAT-N-SH2 Fusion Protein Gene Expression Vector or Recombinant Plasmid pET-22b(+)-TAT-N-SH2

1) Design and Synthesis of TAT-N-SH2

According to the preferred codons of *Escherichia coli*, the amino acid sequences of TAT and N-SH2 were converted into gene sequences, and the gene sequences of TAT and N-SH2 were connected with the BamHI Restriction Enzyme cutting site, and the Nde I Restriction Enzyme cutting site was added at the 5' end. A stop codon TGA and a SalI Restriction Enzyme cutting site were added to the 3' end to synthesize the TAT-N-SH2 gene. Its nucleotide sequence is as follows:

```
                                                          (SEQ ID NO.: 9)
CATATG---tac ggc cgc aag aaa cgc cgc cag cgc cgc cgc---GGATCC--aga tgg ttt cac
  Nde I              TAT penetrating sequence               BamHI cca aat atc act ggt gtg gag gca gaa aac cta ctg ttg aca aga gga gtt gat ggc agt ttt ttg gca aga cct agt aaa agt aac cct gga gac ttc aca ctt tcc gtt aga aga aat gga gct gtc acc cac atc aag att cag aac act ggt gat tac tat gac ctg tat gga ggg gag aaa ttt gcc act ttg gct gag ttg gtc cag tat tac atg gaa cat cac ggg caa tta aaa gag aag aat gga gat gtc att gag ctt aaa tat cct ctg aac TGA---GTCGAC
                            Stop     Sal I
```

Send the company to synthesize the above TAT-N-SH2 gene.

2) Identification of Expression Vector pET-22b(+)-TAT-N-SH2

The recombinant plasmid pET-22b(+)-TAT-N-SH2 was transformed into BL21 competent cells, and after culturing in a 37° C. incubator for 12 hours, a monoclonal colony was picked and inoculated in LB medium containing 100 mg/L ampicillin, after culturing at 37° C. on a shaker, harvesting bacteria and extracting plasmids, double digested with NdeI and SalI, and identified by agarose gel electrophoresis. The expected 342 bp insert was obtained (FIG. 1). The DNA sequencing results (FIG. 2) show that it is consistent with the synthesized sequence. pET The −22b(+)-TAT-N-SH2 recombinant plasmid was constructed successfully.

The obtained recombinant plasmid pET-22b(+)TAT-SHP2-N-SH2 was double digested with Nde I and Sal I enzymes, and then subjected to agarose gel electrophoresis. The red arrow is the target fragment.

2. Expression of Recombinant TAT-N-SH2 Fusion Protein

The recombinant plasmid pET-22b(+)-TAT-N-SH2 was transformed into *Escherichia coli* BL21 competent cells, and after culturing in a 37° C. incubator for 12 hours, the colonies with neat edges and good growth status were picked and inoculated into in LB medium containing 100 mg/L ampicillin, the shaker was incubated at 37° C. overnight; the next day, inoculated in a fresh LB medium containing 100 mg/L ampicillin at a ratio of 1:100, and continued to culture at 37° C. until the bacterial density reached OD600=0.4-0.6, adding 0.01-0.1 mM IPTG for 4 h induction, centrifuged at 12,000 rpm for 20 min to collect bacteria, and stored at −20° C.

3. Purification of Recombinant TAT-N-SH2 Fusion Protein

1) Weigh the bacterial solution, add pH 6.5 PB lysis buffer at a ratio of 1:7, and place it in a 4° C. refrigerator to stir evenly until dissolved; at a power of 300 W, the working time is 5 s, the gap time is 10 s, and ultrasound in ice bath for 20 min; 4° C., 12000 rpm centrifugation for 20 min, collect the supernatant;

2) Take 25 mL of the supernatant of the split bacteria and put it into the dialysis bag prepared in advance, use 30 times the volume of the equilibrium solution A (20 mM pH 6.5, PB) as the outer solution, stir and dialyze at 4° C. overnight, and centrifuged at 12000 rpm for 20 min at 4° C., collect the supernatant and pass it through a 0.22 μm filter membrane, and record the volume; take a 25 mL SP-cation exchange chromatography column packed in advance, equilibrate the column with equilibration A solution until the baseline is stable, and adjust to zero, the sample was loaded at a flow rate of 1 mL/min, collect the peaks that pass through, and stop peaking when the baseline is stable; at a flow rate of 1.5 mL/min, use equilibrated solution A and elution solution B (20 mM pH (5.4, 6.5, 7.4) PB, 1 M NaCl) for 0-100% linear elution, and collect elution peak 4; The elution peak of the target protein was dialyzed with 30-fold volume of PBS. After dialysis, filter and sterilize with a 0.22 μm filter membrane to obtain the target protein TAT-N-SH2 fusion protein.

4. Identification of the Induction Expression and Purification Results of Recombinant TAT-N-SH2 Fusion Protein 1) Use SDS-PAGE (polyacrylamide gel electrophoresis) to analyze the expression of the target protein (as shown in FIG. 3). Compared with the uninduced group, the induced group has specific protein bands, and the size corresponds to the theoretical molecular weight (12.870 KD).

After ultrasonic bacteria splitting, the supernatant and the precipitate were collected respectively, and SDS-PAGE was used to detect whether the target protein was expressed in the supernatant. The results are shown in FIG. 4, the target protein is present in both the supernatant and the precipitate of the split bacteria, but compared with the split bacteria supernatant, the amount of the split bacteria precipitate is very small and can be ignored. Therefore, in the follow-up experiments, we all have the supernatant of the split bacteria as the raw material for fine separation.

The lysed supernatant, which has been crudely extracted by split bacteria, is dialyzed and centrifuged, and then further separated by SP-cation exchange chromatography. Collect peaks at different detection wavelengths, finally, it is found that the target protein can only be detected at the wavelength of 215 nm, and a total of 1 pass-through peak and 4 elution peaks are received, namely: pass-through peak, SP peak 1, SP peak 2, SP peak 3, SP peak 4 (as shown in FIG. 5); each peak is analyzed by SDS-PAGE, and the peak of the target protein is detected as SP4 (as shown in FIG. 6).

5. Identification of the Specificity and Purity of Recombinant TAT-N-SH2 Fusion Protein After qualitative detection of the target protein by Western-blot, it is found that the rabbit anti-human SHP2 polyclonal antibody can specifically bind to the target protein (as shown in FIG. 7), it is proved that the purified protein is the target protein.

The purified fusion protein was detected by HPLC, 20 μL of sample was injected into the needle, the running time was 20 min, the flow rate was 0.8 mL/min, the detection wavelength was 280 nm, and the area of the main peak was used to determine the purity of the sample. The results show that the purity of the fusion protein is 95.92% (FIG. 8).

Example 2 Fusion Polypeptides of Four TAT Penetrating Peptides and the ITIM Motif Binding Region of the C-Terminal SH2 Domain of SHP2

1. A Fusion Polypeptide of a TAT Penetrating Peptide and the ITIM Motif Binding Region of the C-Terminal SH2 Domain of SHP2, Characterized in That the TAT Penetrating Peptide and the ITIM Motif-Binding Region of C-SH2 are Linked by two Prolines (TAT-C-SH2), and the Connection Method is: TAT-Phe-Phe-C-SH2; its Amino Acid Sequence is as Follows:

(SEQ ID NO.: 5)
YGRKKRRQRRR-*PP*-VRESQSHPGDFVL

All L-type amino acids were used and sent to the company to synthesize the above-mentioned TAT-C-SH2 polypeptide (named L1). Taking the sequence of polypeptide L1 as a reference, the inverse sequences of L1 were synthesized, respectively, the L1 sequence synthesized with D-type amino acid, and the L1 inverse sequence synthesized with D-type amino acid were named L2, D1, and D2, respectively. Its amino acid sequence is as follows:

```
1) inverse L-type polypeptide (L2):
                        (SEQ ID NO.: 6)
LVFDGPHSQSERVPPRRRQRRKKRGY 2) D-type polypeptide (D1):
                        (SEQ ID NO.: 7)
YGRKKRRQRRRPPVRESQSHPGDFVL 3) inverse D-type polypeptide (D1):
                        (SEQ ID NO.: 8)
LVFDGPHSQSERVPPRRRQRRKKRGY
```

All sent to the company for chemical synthesis.

2. Identification of Peptides

The purity of the synthesized polypeptide was analyzed by HPLC, 20 μL of sample was injected into the needle, the running time was 20 min, the flow rate was 1.0 mL/min, the detection wavelength was 220 nm, and the area of the main peak was used to determine the purity of the sample. The results show that the purity of L1 polypeptide is 96.74% (FIG. 9A), the purity of L2 polypeptide is 98.1% (FIG. 9B), the purity of D1 polypeptide is 99.27% (FIG. 9C), and the purity of D2 polypeptide is 96.66% (FIG. 9D).

The molecular weight of the synthesized polypeptides was detected by mass spectrometry. The results show that: the molecular weight of L1 polypeptide is 3206 (FIG. 10A), the molecular weight of L2 polypeptide is 3206.67 (FIG. 10B), the molecular weight of D1 polypeptide is 3206.63 (FIG. 10C), and the molecular weight of D2 polypeptide is 3206.79 (FIG. 10D), which is consistent with the theoretical molecular weight.

The results show that the successful synthesis of the peptide can be used for further in vitro and in vivo experimental research.

Example 3 the Penetrating Peptide TAT can Assist Recombinant Fusion Proteins and Polypeptides into T Lymphocytes The ability of recombinant TAT-N-SH2 fusion proteins and polypeptides to enter T lymphocytes is the precondition for their binding to the inhibitory receptor intracellular segment ITIM on their cell membranes. The penetrating peptide TAT is a positively charged short peptide, which can assist various substances to pass through the cell membrane to exert their biological functions. In order to detect whether fusion proteins and polypeptides containing TAT penetrating sequences can enter T lymphocytes, we labeled TAT-N-SH2 fusion protein, L1 polypeptide and control peptide with FITC, and observed their entry into T lymphocytes by confocal microscopy, the action time was 0, 0.5, 4, 24, 72, 96, 120 and 144 h (FIG. 11). The results show that most of the fusion proteins with TAT penetrating sequence enter T cells within 24 h, and have gradually weakened until 120 h (FIG. 11c). However, most of the L1 peptides with TAT penetrating sequence has entered T cells within 0.5 h, and gradually weakened until 72 h (FIG. 11b); the control peptide without TAT penetrating sequence can not enter T cells (FIG. 11a). This result indicates that the TAT penetrating sequence can assist fusion proteins and polypeptides into the target cells, and the time of entry of polypeptides and fusion proteins into T cells is different, which may be related to their molecular weights.

Example 4 Effects of Recombinant Fusion Proteins and Polypeptides on T Lymphocyte Function 1. Effects of Recombinant TAT-N-SH2 Fusion Protein and L1 (TAT-SHP2-C-SH2) Polypeptide on T Lymphocyte Proliferation To test whether recombinant TAT-N-SH2 fusion protein and L1 (TAT-SHP2-C-SH2) polypeptide can enhance the proliferation of T lymphocytes, we used 80 μg/mL TAT-SHP2-N-SH2 fusion protein and TAT-SHP2-C-SH2 polypeptide to stimulate T lymphocytes for 3 days, respectively, the proliferation of T lymphocytes was detected by CFSE. The results show that the proliferation rate of T lymphocytes in the control group is 62.83% (FIG. 12a). The proliferation rate of T lymphocytes in the recombinant TAT-N-SH2 fusion protein group is 61.05% (FIG. 12b) and the proliferation rate of T lymphocytes in the L1 (TAT-SHP2-C-SH2) polypeptide group is 60.33% (FIG. 12c). The statistical results show that compared with the control group, the recombinant TAT-N-SH2 fusion protein and L1 polypeptide do not significantly increase the proliferation of T lymphocytes (FIG. 12d), which indicates that the recombinant TAT-N-SH2 fusion protein and L1 (TAT-SHP2-C-SH2) polypeptide has no effect on T lymphocyte proliferation.

2. Effects of Recombinant TAT-N-SH2 Fusion Protein and L1 (TAT-SHP2-C-SH2) Polypeptide on Apoptosis of T Lymphocytes T lymphocytes were stimulated with recombinant TAT-N-SH2 fusion protein and L1 polypeptide for 3 days and the apoptosis of T lymphocytes in different treatment groups was detected by flow cytometry. FIG. 13 a-d shows the effect of Annexin V-FITC detection peptide on T lymphocyte apoptosis, resuspended cells were added to different groups to treat untreated groups SHP2-NC, SHP2-N-SH2

(80 μg/mL), TAT-SHP2-C-SH2 polypeptide (80 μg/mL) and then continue to culture on EASY-T-stimulated culture plates (add 50 ng PD-L1 antibody 3 hours before adding cell mixture to coat 24-well plate at 37° C.) for 3 days, cells were collected and stained with FITC and PI for detection by flow cytometry. FIG. 13e, according to the results of flow cytometry, the proportion of apoptotic cells was counted, compared with the control group, *p<0.05 or **p<0.01. In conclusion, compared with the control group, the apoptosis of T lymphocytes in the groups treated with recombinant TAT-N-SH2 fusion protein and L1 polypeptide is significantly decreased.

3. Effects of Recombinant TAT-N-SH2 Fusion Protein and L1 (TAT-SHP2-C-SH2) Polypeptide on the Phosphorylation Level of Downstream Signaling Molecules Mediated by T Lymphocytes The T lymphocytes stimulated by recombinant TAT-N-SH2 fusion protein and L1 (TAT-SHP2-C-SH2) polypeptide for 3 days were collected to detect the changes in the phosphorylation levels of ERK, AKT and JNK molecules. The results show that compared with the untreated group, the expression levels of ERK, AKT and JNK do not change significantly, but the expression levels of p-ERK and p-AKT in the TAT-SHP2-N-SH2 fusion protein stimulation group have the most obvious changes and the expression level of p-AKT has changed most obviously in the TAT-SHP2-C-SH2 polypeptide stimulation group (FIG. 14, a-d).

4. Effects of Recombinant TAT-N-SH2 Fusion Protein and L1 (TAT-SHP2-C-SH2) Polypeptide on Cytokine IL-2 Secreted by T Lymphocytes The T lymphocytes stimulated by recombinant TAT-N-SH2 fusion protein and L1 polypeptide for 3 days were collected to detect the level of cytokine IL-2 secreted. The results show that, compared with the control group, through TAT-SHP2-N-SH2 fusion protein and SHP2-C-SH polypeptide stimulation, the level of IL-2 secreted by T lymphocytes is significantly increased (FIG. 15).

Example 5 Study on the Direct Killing Ability of Recombinant TAT-N-SH2 Fusion Protein and L1 (TAT-SHP2-C-SH2) Polypeptide on Tumor Cells In order to detect whether the recombinant TAT-N-SH2 fusion protein and L1 polypeptide have direct killing effect on tumor cells, we co-cultured different concentrations (20 μg/mL, 40 μg/mL, 80 μg/mL) of recombinant TAT-N-SH2 fusion protein and L1 polypeptide with tumor cells MDA-MB-231 and SW480, and applied zenCell owl live cell dynamic imaging analysis system to observe its effect on tumor cells in real time. The experimental results show that, compared with the untreated group, the recombinant TAT-N-SH2 fusion protein and L1 polypeptide have no direct toxic effect on tumor cells MDA-MB-231 and SW480, which indicates that the recombinant TAT-N-SH2 fusion protein and L1 polypeptides play a role in killing tumor cells by acting on T cells (FIG. 16).

Example 6 Study on Recombinant Fusion Proteins and Polypeptides to Enhance the Killing Ability of T Cells on Tumor Cells In Vitro 1. The Effect of Recombinant TAT-N-SH2 Fusion Protein on T Cells Killing Breast Cancer Cells MDA-MB-231 and Colon Cancer Cells SW480

Three protein concentrations (20 μg/mL, 40 μg/mL, 80 μg/mL) of TAT-SHP2-N-SH2 fusion protein were selected to stimulate human T lymphocytes and the killing effect on tumor cells MDA-MB-231 and SW480, respectively at an effector-target ratio of 30:1 was detected by CytoTox 96 non-radioactive cytotoxicity assay. The experimental results show that when the target cells are breast cancer cell line MDA-MB-231, the killing effect of TAT-SHP2-N-SH2 fusion protein groups at concentrations of 40 μg/mL and 80 μg/mL is significantly higher than that of the control group (p=0.0379 and p=0.0367). When the target cells are colon cancer cell line SW480, the protein groups at three concentrations are all significantly higher than the non-administered groups (untreated group) (FIG. 17, Table 1). It shows that TAT-SHP2-N-SH2 fusion protein can enhance the effect of T cells in killing tumor cells, and the effect of killing colon cancer cells is better than that of breast cancer cells.

TABLE 1

Killing effect of T cells stimulated by TAT-SHP2-N-SH2 fusion protein on different tumor cell lines

| | Cytotoxicity (%) | |
|---|---|---|
| Groups | MDA-MB-231 | SW480 |
| PBS | 8.2 ± 3.197 | 6.433 ± 4.504 |
| SHP2-N-SH2 (80 μg/ml) | 21.78 ± 3.021* | 50.64 ± 2.068*** |
| PBS | 2.61 ± 1.172 | 5.36 ± 3.219 |
| SHP2-N-SH2 (40 μg/ml) | 12.55 ± 3.037* | 44.42 ± 5.78** |
| PBS | 3.297 ± 1.645 | 2.353 ± 1.441 |
| SHP2-N-SH2 (20 μg/ml) | 15.11 ± 6.483$^{ns}$ | 23.51 ± 1.432*** |

Compared with the untreated group,
*p < 0.05 or
**p < 0.01 or
***p < 0.001,
p > 0.05 is not statistically significant 2. The Effect of L1 (TAT-SHP2-C-SH2) Polypeptide on T Cells Killing Breast Cancer Cells MDA-MB-231 and Colon Cancer Cells SW480

CytoTox 96 non-radioactive cytotoxicity assay was used to detect the killing effect of human T lymphocytes stimulated by TAT-SHP2-C-SH2 polypeptide (20 μg/mL, 40 μg/mL, 80 μg/mL) for 4 days on tumor cell lines MDA-MB-231 and SW480, respectively. When the effector-target ratio was 30:1 and the TAT-SHP2-C-SH2 polypeptide concentrations were 40 μg/mL and 80 μg/mL, respectively, compared with the control group, the ability of T lymphocytes stimulated with TAT-SHP2-C-SH2 polypeptide to kill MDA-MB-231 and SW480 is significantly enhanced (FIG. 18, Table 2).

TABLE 2

Killing effect of T cells stimulated by TAT-SHP2-C-SH2 polypeptide on different tumor cell lines

| | Cytotoxicity (%) | |
|---|---|---|
| Groups | MDA-MB-231 | SW480 |
| PBS | 3.887 ± 3.887 | 6.433 ± 4.504 |
| SHP-C-SH2 (80 μg/ml) | 34.8 ± 7.424* | 40.19 ± 8.373* |
| PBS | 1.003 ± 0.6353 | 5.36 ± 3.219 |
| SHP2-C-SH2 (40 μg/ml) | 20.55 ± 1.157*** | 31.38 ± 3.779** |
| PBS | 3.15 ± 1.774 | 2.353 ± 1.441 |
| SHP2-C-SH2 (20 μg/ml) | 5.933 ± 3.955$^{ns}$ | 20.24 ± 8.943$^{ns}$ |

Compared with the untreated group,
*p < 0.05 or
**p < 0.01 or
***p < 0.001,
p > 0.05 is not statistically significant.

3. The Effect of L1, L2, D1, D2 Polypeptides on the Killing of Lung Cancer Cells 11460 by T Cells CytoTox 96 non-radioactive cytotoxicity assay was used to detect the killing effect of L1, L2, D1 and D2 polypeptides (40 μg/mL) on lung cancer cells H460 after stimulating human T lymphocytes for 4 days, respectively. When the effector-target ratio is 20:1, compared with the untreated group and the control peptide, the ability of T lymphocytes stimulated by L1, L2, D1, and D2 polypeptides to kill lung cancer cells H460 is significantly improved, and the D2 polypeptide has the strongest effect. (FIG. 19, Table 3).

TABLE 3

The killing effect of T cells stimulated by L1, L2, D1 and D2 polypeptides on lung cancer cells H460.

| Groups | Cytotoxicity (%) |
|---|---|
| PBS | $9.87 \pm 0.41$ |
| R | $12.51 \pm 1.91^{\#\#\#\#}$ |
| L1 | $33.23 \pm 2.32^{****\#\#}$ |
| L2 | $27.46 \pm 2.39^{***\#\#\#}$ |
| D1 | $39.43 \pm 1.31^{****\#\#}$ |
| D2 | $47.62 \pm 2.70^{****}$ |

Compared with the control group,
$^*P < 0.05$,
$^{**}P < 0.01$,
$^{***}P < 0.001$,
$^{****}P < 0.0001$;
Compared with group D2,
$^{\#}P < 0.05$,
$^{\#\#}P < 0.01$,
$^{\#\#\#}P < 0.001$

Example 7 Antitumor Effects of Recombinant Fusion Proteins and Polypeptides In Vivo

1. Detection of Antitumor Effect of Recombinant TAT-N-SH2 Fusion Protein on Mouse Colon Cancer A subcutaneous tumor model of MC38 colon cancer mice was established. The dose of 50 μg/mouse αPD-1 antibody was used as the positive control drug, and select the TAT-SHP2-N-SH2 fusion protein with a concentration of 1.25 μg/mouse (N1.25), 2.5 μg/mouse (N2.5), 5 μg/mouse (N5) and 10 μg/mouse (N10) by intraperitoneal injection. After 8 administrations, the tumor-bearing mice were dissected and weighed, and it is found that the tumor weight in the TAT-SHP2-N-SH2 fusion protein group is significantly smaller than that in the control group, and the tumor weight in the N5 group is smaller than that in the αPD-1 antibody group (FIG. 20, a-b), the N5 group has the highest tumor inhibition rate (Table 4), reaching 80.9%. The results indicate that the 5 μg/mouse TAT-SHP2 1-N-SH2 fusion protein has the best effect in inhibiting colon cancer tumors.

TABLE 4

Tumor inhibition rate of TAT-SHP2-N-SH2 fusion protein on colon cancer tumor-bearing mice

| | Tumor weight (g) | Tumor inhibition rate % |
|---|---|---|
| Control | $0.81 \pm 0.11$ | |
| αPD-1 | $0.44 \pm 0.06^*$ | 45.9 |
| N1.25 | $0.36 \pm 0.11^*$ | 55.3 |
| N2.5 | $0.38 \pm 0.11^*$ | 53.5 |

TABLE 4-continued

Tumor inhibition rate of TAT-SHP2-N-SH2 fusion protein on colon cancer tumor-bearing mice

| | Tumor weight (g) | Tumor inhibition rate % |
|---|---|---|
| N5 | $0.16 \pm 0.03^{***}$ | 80.9 |
| N10 | $0.34 \pm 0.08^{**}$ | 57.8 |

Compared with Control group,
$^*p < 0.05$,
$^{**}p < 0.01$,
$^{***}p < 0.001$

2. Detection of Antitumor Effect of L1 (TAT-SHP2-C-SH2) Polypeptide on Mouse Colon Cancer The effect of TAT-SHP2-C-SH2 polypeptide on tumor growth in mice was evaluated by the established MC38 colon cancer mouse subcutaneous tumor-bearing model, administered by intraperitoneal injection of 1.25 μg/mouse (C1.25), 2.5 μg/mouse (C2.5), 5 μg/mouse (C5) and 10 μg/mouse (C10) TAT-SHP2-C-SH2 polypeptide and at the same time, a dose of 50 μg/mouse αPD-1 antibody (αPD-1) was used as the positive control drug and adding TAT-SHP2-N-SH2 (5 μg/mouse) group and a combination group (TAT-SHP2-N-SH2 fusion protein and TAT-SHP2C-SH2 polypeptide, each 5 μg/mouse), it is found that compared with the control group, TAT-SHP2-C-SH2 polypeptide group, αPD-1 antibody group, TAT-SHP2-N-SH2 fusion protein group and combination group, the tumor weight is significantly reduced. In addition, the combination group has the best tumor inhibitory effect, followed by the N5 group, and the TAT-SHP2-C-SH2 polypeptide at a dose of 5 μg/mouse has the slowest tumor growth (FIG. 21, a-b); the combination group has the best tumor inhibition rate, followed by the N5 group (Table 5). The results show that different dose groups have inhibitory effects on the growth of mouse tumors, and the combination group has the best effect.

TABLE 5

Tumor inhibition rate of TAT-SHP2-C-SH2 polypeptide on colon cancer tumor-bearing mice

| | Tumor weight (g) | Tumor inhibition rate % |
|---|---|---|
| Control | $1.12 \pm 0.08$ | |
| C1.25 | $0.34 \pm 0.09^{***}$ | 60.2 |
| C2.5 | $0.44 \pm 0.09^{***}$ | 70 |
| C5 | $0.34 \pm 0.05^{***}$ | 72.8 |
| C10 | $0.36 \pm 0.09^{***}$ | 70.6 |
| αPD-1 | $0.38 \pm 0.14^{***}$ | 69.2 |
| N5 | $0.26 \pm 0.07^{***}$ | 77.1 |
| N5 + C5 | $0.24 \pm 0.07^{***}$ | 80.4 |

Compared with the Control group,
$^{***}p < 0.001$

3. Detection of Antitumor Effect Effect of Recombinant TAT-N-SH2 Fusion Protein and L1 (TAT-SHP2-C-SH2) Polypeptide on Mouse Breast Cancer We further evaluated the effects of TAT-SHP2SHP2-N-SH2 fusion protein and TAT-SHP2SHP2-C-SH2 polypeptide on tumor growth in mice by establishing a subcutaneous tumor-bearing model of EMT breast cancer mice. We used TAT-SHP2SHP2-C-SH2 polypeptide at 5 μg/mouse (C5), 10 μg/mouse (C10), 15 μg/mouse (C15) and 2 μg/mouse (N2), 5 μg/mouse (N5), 10 μg/mouse (N10), 15 μg/mouse (N15) of TAT-SHP2SHP2-N-SH2 fusion protein were administered by intraperitoneal injection and at the same time, the dose of 50 µg/mouse αPD-1 antibody (αPD-1) was used as the positive control drug. The results show that: The tumor volume of each treatment group in TAT-SHP2SHP2-C-SH2 polypeptide group, αPD-1 antibody group, and TAT-SHP2SHP2-N-SH2 fusion protein group is significantly smaller than that in the control group; TAT-SHP2SHP2-N-SH2 fusion protein (5 µg/mouse) and TAT-SHP2SHP2 or SHP1-C-SH2 polypeptide (5 µg/mouse) groups have the smallest tumor weight and the best tumor inhibition rate (FIG. 22, a-b, Table 6). The results indicate that different dose groups have inhibitory effects on the growth of mouse tumors, and the fusion protein and polypeptide doses are both 5 µg/mouse with the best effect, which is consistent with the results of colon cancer tumor suppression.

TABLE 6

Tumor inhibition rate of TAT-SHP2-N-SH2 fusion protein and TAT-SHP2-C-SH2 polypeptide on breast cancer tumor-bearing mice

|  | Tumor weight (g) | Tumor inhibition rate % |
|---|---|---|
| Control | $1.24 \pm 0.21$ | |
| C5 | $0.44 \pm 0.12^{**}$ | 64.6 |
| C10 | $0.52 \pm 0.13^{*}$ | 57.6 |
| C15 | $0.50 \pm 0.07^{**}$ | 59.4 |
| N2 | $0.56 \pm 0.11^{*}$ | 54.9 |
| N5 | $0.37 \pm 0.10^{**}$ | 70.3 |
| N10 | $0.46 \pm 0.12^{**}$ | 63 |
| N15 | $0.64 \pm 0.15^{*}$ | 47.9 |
| αPD-1 | $0.52 \pm 0.12^{*}$ | 58.3 |

Compared with control group,
$^{*}p < 0.05$,
$^{**}p < 0.01$,
$^{***}p < 0.001$

4. Inhibitory Effect of Recombinant TAT-N-SH2 Fusion Protein and L1 (TAT-SHP2-C-SH2) Polypeptide on Transplanted Tumors in Nude Mice 1) Inhibitory Effect of Recombinant TAT-N-SH2 Fusion Protein and L1 (TAT-SHP2-C-SH2) Polypeptide on MC38 Colon Cancer Nude Mice In order to exclude the direct inhibitory effect of recombinant TAT-N-SH2 fusion protein and L1 (TAT-SHP2-C-SH2) polypeptide on tumors, we selected immunodeficient nude mice to inoculate MC38 colon cancer tumors, and started administration 14 days after tumor formation, 4 days to measure the tumor volume, after 30 days, the mice were sacrificed for dissection, and the tumor weight was measured. It is found that the the tumor volume, tumor weight and tumor inhibition rate of recombinant TAT-N-SH2 fusion protein and L1 (TAT-SHP2-C-SH2) polypeptide mice are not significantly different from those in the control group (FIG. 23, a-c, Table 7), which indicates that TAT-SHP2-N-SH2 fusion protein and TAT-SHP2-C-SH2 polypeptide have no direct inhibitory effect on colon cancer.

TABLE 7

Antitumor effect of recombinant TAT-N-SH2 fusion protein and L1 polypeptide on colon cancer nude mice

|  | Tumor weight (g) | Tumor inhibition rate % |
|---|---|---|
| Control | $0.30 \pm 0.07$ | |
| C5 | $0.25 \pm 0.06^{ns}$ | 6.3 |
| N5 | $0.25 \pm 0.06^{ns}$ | 9.9 |

Compared with Control group,
$^{ns}p > 0.05$

2) Antitumor Effect of Recombinant TAT-N-SH2 Fusion Protein and L1 (TAT-SHP2-C-SH2) Polypeptide on EMT-6 Breast Cancer Nude Mice At the same time, we selected immune-deficient nude mice to inoculate EMT-6 breast cancer tumors. After 5 days of tumor formation, they were randomly divided into three groups with 6 mice in each group. Start the administration, the administration dose is the same as above, administered once every other day for a total of 8 doses, 4 days to measure tumor size, the growth curve was drawn, and the mice were sacrificed to measure the body weight on day 21. It is found that compared with the control group, there is no significant difference in tumor volume, tumor weight and tumor inhibition rate between the recombinant TAT-N-SH2 fusion protein and L1 (TAT-SHP2-C-SH2) polypeptide treatment group. The results indicate that the recombinant TAT-N-SH2 fusion protein and L1 (TAT-SHP2-C-SH2) polypeptide can not directly inhibit tumor cells, but it inhibits breast cancer tumor growth through immune cells (FIG. 24, a-c, Table 8).

TABLE 8

Tumor inhibition rate of recombinant TAT-N-SH2 fusion protein and L1 polypeptide on breast cancer in nude mice

|  | Tumor weight (g) | Tumor inhibition rate % |
|---|---|---|
| Control | $0.90 \pm 0.13$ | |
| C5 | $0.81 \pm 0.10^{ns}$ | 9.8 |
| N5 | $0.82 \pm 0.13^{ns}$ | 8.3 |

Compared with Control group,
$^{ns}p > 0.05$

5. Detection of Tumor Inhibition Effect of Recombinant TAT-N-SH2 Fusion Protein and L1 (TAT-SHP2-C-SH2) Polypeptide on Mouse PD-L1 Knockout Breast Cancer Xenografts Recombinant TAT-N-SH2 fusion protein and L1 (TAT-SHP2-C-SH2) polypeptide target the ITIM motif of inhibitory receptors. Therefore the therapeutic range thereof is wider than that of PD-1 monoclonal antibodies that block PD-1, an inhibitory receptor and it is theoretically possible to treat tumors that do not respond to PD-1 antibody therapy. To this end, we constructed a breast cancer EMT-6 cell line stably knocked out PD-L1 (PD-L1-KO-EMT6), inoculated into the mouse mammary fat pad, and the recombinant TAT-N-SH2 fusion protein (N5) and TAT-SHP2-C-SH2 polypeptide (C5) were administered by intraperitoneal injection at 5 µg/mouse, respectively and at the same time, a dose of 50 µg/mouse αPD-1 antibody (αPD-1) was used as the control drug. The results show that both N5 and C5 can significantly inhibit the growth of PD-L1-KO-EMT6 tumors, but PD-1 antibody treatment is ineffective (FIG. 25, a-c, Table 9).

TABLE 9

Tumor inhibition rates of different drugs on PD-L1-knockout
EMT-6 subcutaneous xenografts in BALB/c mice

| Groups | Tumor weight (g) | Tumor inhibition rate (%) |
|---|---|---|
| negative control | 0.85 ± 0.23 | |
| N5 | 0.34 ± 0.20** | 60.5% |
| C5 | 0.58 ± 0.15* | 31.9% |
| αPD-1 | 0.45 ± 0.25* | 47.7% |

Compared with the control group,
**P < 0.01,
*P < 0.05

6. Detection of Tumor-Inhibitory Effect of L1, L2, D1, D2 Polypeptides on Mouse Lung Cancer We further evaluated the effects of L1, L2, D1 and D2 polypeptides on tumor growth in mice through the established mouse Lewis lung cancer xenograft model. We administered L1, L2, D1 and D2 polypeptides by intraperitoneal injection of 5 μg/mouse respectively. At the same time, the dose of 5 μg/mouse control peptide (R peptide) was used as the negative control drug, and the normal saline was used as the blank control group (NC), which was administered once every other day. A total of 8. The results show that: L1, L2, D1, and D2 polypeptides can significantly inhibit the growth of tumors. The D2 group has the best tumor inhibition effect and the strongest tumor inhibition rate (P<0.001), which is consistent with the results of the in vitro killing experiments (FIG. 26, a-c, Table 10).

TABLE 10

Antitumor effect of L1, L2, D1, D2
polypeptides on mouse lung cancer

| Groups | dose | Tumor weight (g) | Tumor inhibition rate (%) |
|---|---|---|---|
| NC | 0.1 ml | 1.56 ± 0.53 | — |
| R | 5 μg | 1.38 ± 0.33#### | 11.54 |
| L1 | 5 μg | 0.73 ± 0.14**#### | 53.21 |
| L2 | 5 μg | 1.05 ± 0.16*#### | 32.70 |
| D1 | 5 μg | 0.53 ± 0.16**# | 66.03 |
| D2 | 5 μg | 0.32 ± 0.10*** | 79.49 |

Compared with the control group,
*P < 0.05,
**P < 0.01,
***P < 0.001;
Compared with group D2,
P < 0.05,
P < 0.01,
P < 0.001,
P < 0.0001

All publications mentioned herein are incorporated by reference as if each individual document was cited as a reference, as in the present application. It should also be understood that, after reading the above teachings of the present invention, those skilled in the art can make various changes or modifications, equivalents of which falls in the scope of claims as defined in the appended claims.

The invention claimed is:

1. A fusion protein comprising the amino acid sequence shown in SEQ ID NO:5, SEQ ID NO:6, SEQ ID NO:7, or SEQ ID NO:8.

2. An isolated polynucleotide encoding the fusion protein of claim 1.

3. A vector comprising the polynucleotide of claim 2.

4. A host cell, wherein the host cell comprises the vector of claim 3 integrated into its genome.

5. A method for producing the fusion protein of claim 1, the method comprising:

culturing a host cell under conditions suitable for protein expression, or isolating the fusion protein, wherein the host cell comprises a vector, the vector comprises a polynucleotide encoding the fusion protein of claim 1, or the host cell comprises a polynucleotide encoding the fusion protein of claim 1.

6. A pharmaceutical composition comprising the fusion protein of claim 1 and a pharmaceutically acceptable carrier.

7. A method of treating a tumor, comprising: administering an effective amount of the fusion protein of claim 1.

8. An in vitro non-therapeutic method for inhibiting tumor cell growth, comprising:

culturing a tumor cell in the presence of the fusion protein of claim 1, thereby inhibiting the tumor cell growth.

9. A host cell, wherein the host cell comprises the polynucleotide of claim 2 integrated into its genome.

10. The method of claim 7, wherein the tumor is selected from the group consisting of breast cancer, colon cancer, lung cancer, colorectal cancer, gastric cancer, esophagus cancer, pancreatic cancer, ovarian cancer, prostate cancer, kidney cancer, liver cancer, brain cancer, melanoma, multiple myeloma, leukemia, lymphoma, head and neck tumor, thyroid cancer, and a combination thereof.

11. A method of treating a tumor, comprising: administering an effective amount of the vector of claim 3, wherein the tumor is selected from the group consisting of breast cancer, colon cancer, lung cancer, colorectal cancer, gastric cancer, esophagus cancer, pancreatic cancer, ovarian cancer, prostate cancer, kidney cancer, liver cancer, brain cancer, melanoma, multiple myeloma, leukemia, lymphoma, head and neck tumor, thyroid cancer, and a combination thereof.

* * * * *